US009991176B2

(12) United States Patent
Mehendale et al.

(10) Patent No.: US 9,991,176 B2
(45) Date of Patent: Jun. 5, 2018

(54) NON-DESTRUCTIVE ACOUSTIC METROLOGY FOR VOID DETECTION

(71) Applicants: Manjusha Mehendale, Morristown, NJ (US); Michael Kotelyanskii, Chatham, NJ (US); Todd W. Murray, Golden, CO (US); Robin Mair, West Chicago, IL (US); Priya Mukundhan, Lake Hopatcong, NJ (US); Jacob D. Dove, Boulder, CO (US); Xueping Ru, Flanders, NJ (US); Jonathan Cohen, Flanders, NJ (US); Timothy Kryman, Flanders, NJ (US)

(72) Inventors: Manjusha Mehendale, Morristown, NJ (US); Michael Kotelyanskii, Chatham, NJ (US); Todd W. Murray, Golden, CO (US); Robin Mair, West Chicago, IL (US); Priya Mukundhan, Lake Hopatcong, NJ (US); Jacob D. Dove, Boulder, CO (US); Xueping Ru, Flanders, NJ (US); Jonathan Cohen, Flanders, NJ (US); Timothy Kryman, Flanders, NJ (US)

(73) Assignees: Rudolph Technologies, Inc., Flanders, NJ (US); The Regents of the University of Colorado, Denver, CO (US)

( * ) Notice: Subject to any disclaimer, the term of this patent is extended or adjusted under 35 U.S.C. 154(b) by 0 days. days.

(21) Appl. No.: 15/515,126

(22) PCT Filed: Sep. 29, 2015

(86) PCT No.: PCT/US2015/052984
§ 371 (c)(1),
(2) Date: Mar. 28, 2017

(87) PCT Pub. No.: WO2016/054067
PCT Pub. Date: Apr. 7, 2016

(65) Prior Publication Data
US 2017/0221778 A1 Aug. 3, 2017

Related U.S. Application Data

(60) Provisional application No. 62/056,773, filed on Sep. 29, 2014.

(51) Int. Cl.
*H01L 21/66* (2006.01)
*G01N 29/06* (2006.01)
(Continued)

(52) U.S. Cl.
CPC ............. *H01L 22/12* (2013.01); *G01N 29/04* (2013.01); *G01N 29/2418* (2013.01);
(Continued)

(58) Field of Classification Search
CPC ..... H01L 22/12; H01L 22/20; G01N 29/2418; G01N 29/46; G01N 29/06; G01N 29/0681; G01N 29/069; G01N 29/07
See application file for complete search history.

(56) References Cited

U.S. PATENT DOCUMENTS

2002/0180445 A1 12/2002 Bertness et al.
2004/0075068 A1 4/2004 Feldman et al.
(Continued)

OTHER PUBLICATIONS

International Search Report and Written Opinion from corresponding International Patent Application No. PCT/US2015/052984, dated Dec. 28, 2015, 9 pages.

*Primary Examiner* — David Zarneke
(74) *Attorney, Agent, or Firm* — Merchant & Gould P.C.

(57) ABSTRACT

Advanced interconnect technologies such as Through Silicon Vias (TSVs) have become an integral part of 3-D integration. Methods and systems and provided for laser-based acoustic techniques in which a short laser pulse
(Continued)

generates broadband acoustic waves that propagate in the TSV structure. An optical interferometer detects the surface displacement caused by the acoustic waves reflecting within the structure as well as other acoustic waves traveling near the surface that has information about the structure dimensions and irregularities, such as voids. Features of voids, such as their location, are also identified based on the characteristics of the acoustic wave as it propagates through the via. Measurements typically take few seconds per site and can be easily adopted for in-line process monitoring.

23 Claims, 18 Drawing Sheets

(51) Int. Cl.
| | | |
|---|---|---|
| | *G01N 29/07* | (2006.01) |
| | *G01N 29/24* | (2006.01) |
| | *G01N 29/46* | (2006.01) |
| | *H01L 21/768* | (2006.01) |
| | *G01N 29/04* | (2006.01) |

(52) U.S. Cl.
CPC ....... *G01N 29/46* (2013.01); *H01L 21/76898* (2013.01); *G01N 29/06* (2013.01); *G01N 29/069* (2013.01); *G01N 29/0681* (2013.01); *G01N 29/07* (2013.01); *G01N 2291/0289* (2013.01); *H01L 22/20* (2013.01)

(56) References Cited

U.S. PATENT DOCUMENTS

| | | | |
|---|---|---|---|
| 2006/0095232 A1 | 5/2006 | Purdy | |
| 2006/0215175 A1 | 9/2006 | Yacoubian | |
| 2008/0216575 A1 | 9/2008 | Klein et al. | |
| 2011/0116084 A1* | 5/2011 | Lee | G01N 21/95684 356/237.1 |
| 2012/0304773 A1* | 12/2012 | Horibe | H01L 21/76898 73/618 |
| 2016/0043008 A1* | 2/2016 | Murray | G01N 29/2418 438/5 |

* cited by examiner

NON-DESTRUCTIVE ACOUSTIC METROLOGY FOR VOID DETECTION

PRIORITY CLAIM

This application is a National Stage Application of International Patent Application No. PCT/US2015/052984, filed Sep. 29, 2015, which claims the benefit of U.S. Provisional Application No. 62/056,773, filed on Sep. 29, 2014, the disclosures of which are incorporated herein by reference in their entirety.

INTRODUCTION

Microelectronics industry trends have continued to move rapidly towards 3-D integration of semiconductor devices and the driving force remains the need for smaller, faster devices with optimized performance, enhanced data transfer speeds, minimum transmission loss, while maintaining reliability and meeting cost targets. Through-silicon via (TSV) technology has entered the mainstream for 3D ICs as they support heterogeneous integration of logic and memory devices resulting in significant improvements in performance. Depending on the application, a "Via-first" or "Via-last" approach may be used in manufacturing. Nevertheless, the process is complex and filling the high aspect ratio vias with copper is one of the most challenging and expensive steps of the fabrication process. Achieving void-free copper fill can be critical to avoiding reliability problems and improving yield. Void formation may occur at the bottom of the vias, along the seamline and at the top of the vias and are dependent on the plating chemistry and approach used.

A conformal or a super conformal (bottom up fill) deposition is employed for filling copper in these high aspect ratio structures and characterization of the vias as-plated, polished and annealed provides useful information to engineers for process optimization. Availability of a non-destructive in-line metrology tool for detection of voids that can provide effective feedback and a faster data turn around while evaluating new plating chemistries is a current need in the industry.

Current methods are mostly destructive and rely on off-line analysis at the feature of interest. Cross-sectional focused ion beam (FIB) SEM is used extensively for the characterization of the voids and although it provides the needed information, it is time consuming and the wafers have to be cleaved for analysis and later scrapped. At-line FIB SEM inspection techniques using a plasma FIB ion mill has been shown to remove material faster (20×) than a liquid metal ion source and have been investigated as an alternative to in-line metrology for the characterization of voids. Additionally, X-ray microscopy with computational tomography has been used to image thermally induced void growth in the same TSVs before and after annealing. However, this technique is also destructive; limited to small sample sizes and requires sample preparation.

In addition to the techniques described above, scanning acoustic microscopy (SAM) has been employed for failure analysis in flip chips. The conventional SAM tools operate in the 5-200 MHz range and can detect gross defects. However, as sample structures decrease in size, inspection becomes challenging with trade-offs made in lateral resolution and depth resolution of defects. With advances in GHz range SAM, studies have shown an improved capability for void detection in TSVs, but these techniques still require the presence of a coupling medium.

Non-Destructive Acoustic Metrology for Void Detection

The present disclosure provides methods and systems for detecting voids in microscopic structures, such as TSV's. In particular examples, a non-contact, non-destructive laser-based ultrasonic technique for detection of voids in TSV structures including those at the bottom of 10:1 aspect ratio structures is provided. Specific vias can be identified for measurements on full wafers and measured during various stages of processing (as-plated, CMP, and anneal).

In one aspect, the technology relates to a method of non-destructive acoustic metrology for void detection in a via in a sample. The method includes generating a model for determining the existence of a void within the via, and generating the model further includes generating a model signal representative of a signal that would be received from performing acoustic metrology on the via; removing a slow signal component due to temperature rise and subsequent heat dissipation from the model signal; generating a model periodogram by performing a Fourier transform over a sliding window; applying a modified image processing segmentation algorithm to locate centroid locations of echo patterns in the model periodogram; and generating a correlation of the centroid locations to a depth of where a model acoustic pulse was reflected within the via. The method further includes directing an excitation laser beam at the via, such that an acoustic wave propagates through the via, and directing a probe laser beam at the via, such that the probe laser beam reflects off the sample, creating a reflected beam encoding data about propagation of the acoustic wave in the via. In addition, the method includes analyzing the reflected beam, using a detection periodogram, to determine one or more detection centroids; applying the generated correlation to determine the depth of an acoustic wave reflection associated with the one or more detection centroids; comparing the determined depth with an expected depth for the via; and based on the comparison of the determined depth with the expected depth, generating an indication that there is the void in the via.

In another aspect, the technology relates to another method of non-destructive acoustic metrology for void detection in a via in a sample, that includes directing an excitation laser beam at the via, such that an acoustic wave propagates through the via, and directing a probe laser beam at the via, such that the probe laser beam reflects off the sample, creating a reflected beam encoding data about propagation of the acoustic wave in the via. The method further includes analyzing the reflected beam, using a periodogram, to identify a first centroid and a second centroid, wherein the first centroid has a first associated delay time and a first associated frequency and the second centroid has a second associated delay time and a second associated frequency, comparing the first and second associated delay times to an expected delay time for an ideally filled via, and comparing the first and second associated frequencies to an expected frequency range. In addition the method includes, based on the comparison of the first and second delay times and the comparison of the first and second associated frequencies, generating an indication that the via contains one or more of the group selected from: a void in a body of the via, a void at the bottom of the via, and no voids.

In yet another aspect, the technology relates to a system for non-destructive acoustic metrology for void detection in a via in a sample. The system includes a first source for generating a excitation beam directed towards the via in the sample; a second source for generating a probe beam directed towards the via in the sample; an optical sensor for detecting a reflected probe beam reflected from the sample; at least one processor; and a memory storing instructions. The instructions stored in the memory, when executed by the at least one processor, perform actions that include generate a model for determining the existence of a void within the via. Generating model includes actions such as generate a model signal representative of a signal that would be received from performing acoustic metrology on the via; remove a slow signal component due to temperature rise and subsequent heat dissipation from the model signal; generate a model periodogram by performing a Fourier transform over a sliding window; apply a modified image processing segmentation algorithm to locate centroid locations of echo patterns in the model periodogram; and generate a correlation of the centroid locations to a depth of where a model acoustic pulse was reflected within the via. The actions further include analyze data associated with the reflected beam, using a detection periodogram, to determine one or more detection centroids; compare features of the one or more detection centroids to expected features of the via to determine if there is a void in the via; and if there is the void in the via, generating an indication that there is the void in the via.

In still another aspect, the technology relates to a substantially void-free integrated circuit device prepared by a process. The process includes manufacturing at least a portion of a first wafer using one or more process tools; receiving the first wafer for inspection, wherein the first wafer includes multiple vias; directing an excitation laser beam at a via of the multiple vias, such that an acoustic wave propagates through the via; and directing a probe laser beam at the via, such that the probe laser beam reflects off the sample, creating a reflected beam encoding data about propagation of the acoustic wave in the via. The process further includes analyzing, using a periodogram, the reflected beam to identify a first centroid and a second centroid, wherein the first centroid has a first associated delay time and a first associated frequency and the second centroid has a second associated delay time and a second associated frequency; comparing the first and second associated delay times to an expected delay time for an ideally filled via; comparing the first and second associated frequencies to an expected frequency range; based on the comparison of the first and second delay times and the comparison of the first and second associated frequencies, determining that the wafer contains at least one void in one or more of the multiple vias. In addition, the process includes, diverting the first wafer from production for additional inspection; modifying the operation of the one or more process tools to produce subsequent wafers that have a lower likelihood of having voids; and manufacturing a second wafer using the modified operation of the one or more process tools to produce the substantially void-free integrated circuit device.

BRIEF DESCRIPTION OF THE DRAWINGS

Non-limiting and non-exhaustive examples are described with reference to the following Figures.

DETAILED DESCRIPTION

In the following detailed description, references are made to the accompanying drawings that form a part hereof, and in which are shown by way of illustrations specific embodiments or examples. These aspects may be combined, other aspects may be utilized, and structural changes may be made without departing from the spirit or scope of the present disclosure. The following detailed description is therefore not to be taken in a limiting sense, and the scope of the present disclosure is defined by the appended claims and their equivalents.

Laser based ultrasonics is a high sensitivity, non-contact technique for the nondestructive evaluation of materials with excellent temporal and spatial resolution. A pulsed laser source irradiates a specimen surface where some of the laser energy is absorbed, leading to local thermal expansion and elastic wave generation through the thermoelastic effect. The amplitude, frequency content, and directivity of the generated acoustic modes depend upon the laser spot size and pulse width, the optical properties of the sample surface, and the thermal and mechanical properties of the heated region. The elastic waves are detected on the sample by monitoring the sample surface displacement, velocity, or reflectivity using a second optical probe. Sensitive optical detection of ultrasound in the MHz-GHz frequency range can be achieved using optical interferometry. Through evaluation of the velocity, dispersion characteristics, scattering, and attenuation of ultrasonic waves, various physical and material properties can be determined. For example, the existence of voids within vias may be identified and the location of the voids may also be determined.

Figure 1:
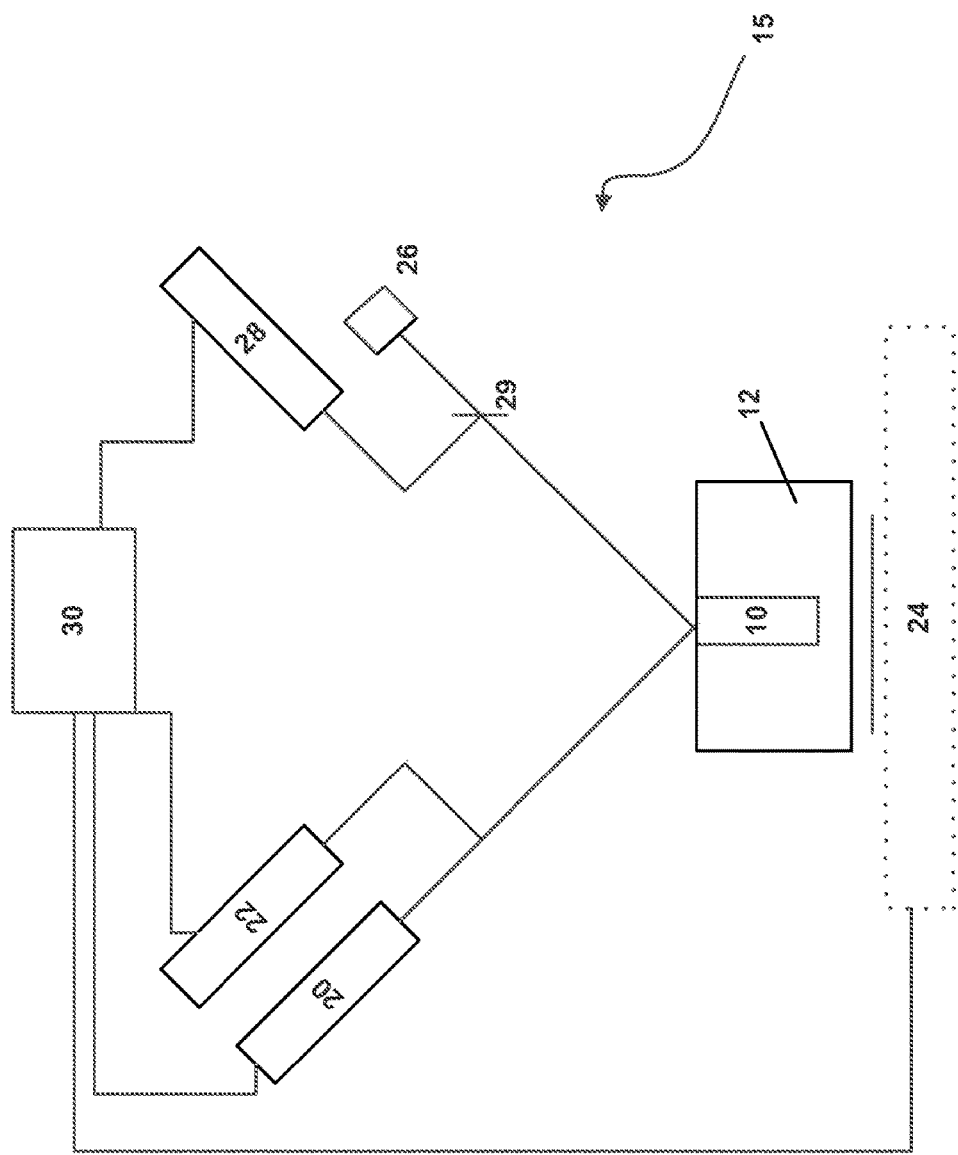
FIG. 1 depicts a schematic of an example of a system suitable for performing void detection through opto-acoustic metrology.

FIG. 1 depicts an example of a system suitable for performing void detection through opto-acoustic metrology. In general this system includes a pump laser 20 (also referred to herein as a excitation laser); a probe laser 22 (also referred to herein as a detection laser); optics including lenses, filters, polarizers and the like (not shown) that direct radiation from the pump and probe lasers 20, 22 to an object 10; a mechatronic support 24 for a substrate/sample 12 of which object 10 is a part, the mechatronic support 24 being adapted to move the substrate 12 relative to the pump and probe lasers 20, 22; a beam dump 26 for capturing radiation from the pump laser returned from the object 10; a sensor 28 adapted to sense an intensity of radiation from the probe laser 22 that is returned from the object 10; and, a controller 30 coupled to the probe and pump lasers 20, 22, the mechatronic support 24, and the sensor 28.

It should be appreciated that the controller 30 may be a self-contained computing device or distributed computing devices capable of performing necessary computations, receiving and sending instructions or commands and of receiving, storing and sending information related to the metrology functions of the system. In examples, the controller includes at least one processor and a memory storing instructions, that when executed by the at least one processor, perform the techniques and methods described herein. Further, the controller may also be connected to peripherals for input/output capabilities. For instance, the controller may be connected to a display or a set of indicators, such as light-emitting diodes (LEDs) that can be displayed or activated in the event of detection of a void or to display other features of the sample or via.

In the depicted embodiment the pump and probe lasers 20, 22 in the embodiment of the opto-acoustic system 15 shown in FIG. 1 can share at least a portion of an optical path to and from the object 10. For example, the lasers can have a number of different relative arrangements including a configuration wherein the paths are the same, partially overlapping, adjacent, or coaxial. In other embodiments, the pump and probe lasers 20, 22 and the beam dump 26 and sensor 28 do not share optical paths. In examples, the pump and probe lasers 20, 22 may be controlled directly so as to obtain the necessary temporal spacing between the pulses of light directed to the object 10.

It should be appreciated that many optical configurations are possible. In some configurations the pump can be a pulsed laser with a pulse width in the range of several hundred femtoseconds to several hundred nanoseconds and the probe beam is a continuous wave (CW) beam coupled to an interferometer or beam deflection system. For example, in systems wherein the probe is pulsed the system can employ a delay stage (not shown) for increasing or decreasing the length of the optical path between the laser and the object 10 associated therewith. The delay stage, where provided, would be controlled by controller 30 to obtain the necessary time delays in the light pulses incident on the object. Many other alternative configurations are also possible. On other embodiments, the system does not include a delay stage. It should be appreciated that the schematic illustration of FIG. 1 is not intended to be limiting, but rather depict one of a number of example configurations for the purpose of explaining the new features of the present disclosure.

In operation the opto-acoustic metrology system 15 directs a series of pulses of light from pump laser 20 to the object 10. These pulses of light are incident (i.e., at an angle which can be any angle between zero to 90 degrees including, for example, 45 degrees and 90 degrees) upon and at least partially absorbed by the object 10. The absorption of the light by the object causes a transient expansion in the material of the object 10. The expansion is short enough that it induces what is essentially an ultrasonic wave that passes down into the object 10 in much the way that sonar waves pass down into a body of water. Light reflected from the object 10 is passed into a beam dump 26, also commonly referred to as a photon detection unit, which extinguishes or absorbs the pump radiation.

In addition to directing the operation of the pump laser 20, the controller 30 directs the operation of the probe laser 22. Probe laser 22 directs radiation in a series of light pulses onto the surface of the object 10 in a time sequence that is intended to intercept the return of the ultrasonic wave to the surface of the object. The interaction of the light pulses from the probe laser 22 with the surface of the object 10 as the ultrasonic waves return to its surface modifies the light pulses from the probe laser which are directed from the object 10 to the sensor 28 by means of beam splitter 29. The sensor 28 may be adapted to sense a change in the intensity of the probe beam of light caused by stress induced changes in the optical characteristics of the object due to transient stress waves passing through the system.

In a configuration where a continuous wave (CW) probe laser is used, an inplane or out of plane displacement of the surface of the sample can be detected using interferometry. Alternatively, the change in surface tilt or change in surface curvature can be analyzed by detecting the beam deflection. Alternatively, or in addition to sensing changes in intensity, the sensor 28 may sense a deflection of the probe beam of light due to physical perturbations in the surface of the object 10 due to transient stress waves intersecting the surface of the object 10. The sensor 28, in one embodiment is a position sensitive device (PSD) that may sense both intensity and deflection.

As discussed above, in one embodiment the focused pump and probe beams are directed to the same spot on the object 10. In another embodiment, the pump and probe beams may be laterally offset from one another, the probe beam preferably being positioned on the object 10. The pump beam may be offset laterally from the probe beam and yet still on the object 10 or positioned adjacent to the object 10. Note that an offset may be achieved by using separate optical paths for the pump and probe beams or by using beams of different wavelengths that are passed through a glass plate that diffracts each beam differently. It may also be desirable to dither one or both of the pump and probe beams to avoid ablation or damage to the surface thereof.

The spot sizes of the pump and probe beams may vary based upon the particular application to which the method is put. The spot sizes of the respective beams may be similar or dissimilar. The spot size of the respective beams may, for example, range from around 100 microns to approximately the wavelength diffraction limit of the optical system used to carry out the optical acoustic metrology process, i.e., to less than 1 micron. The spot size of the laser can be in part based upon the size of the structure being measured.

Figure 2:
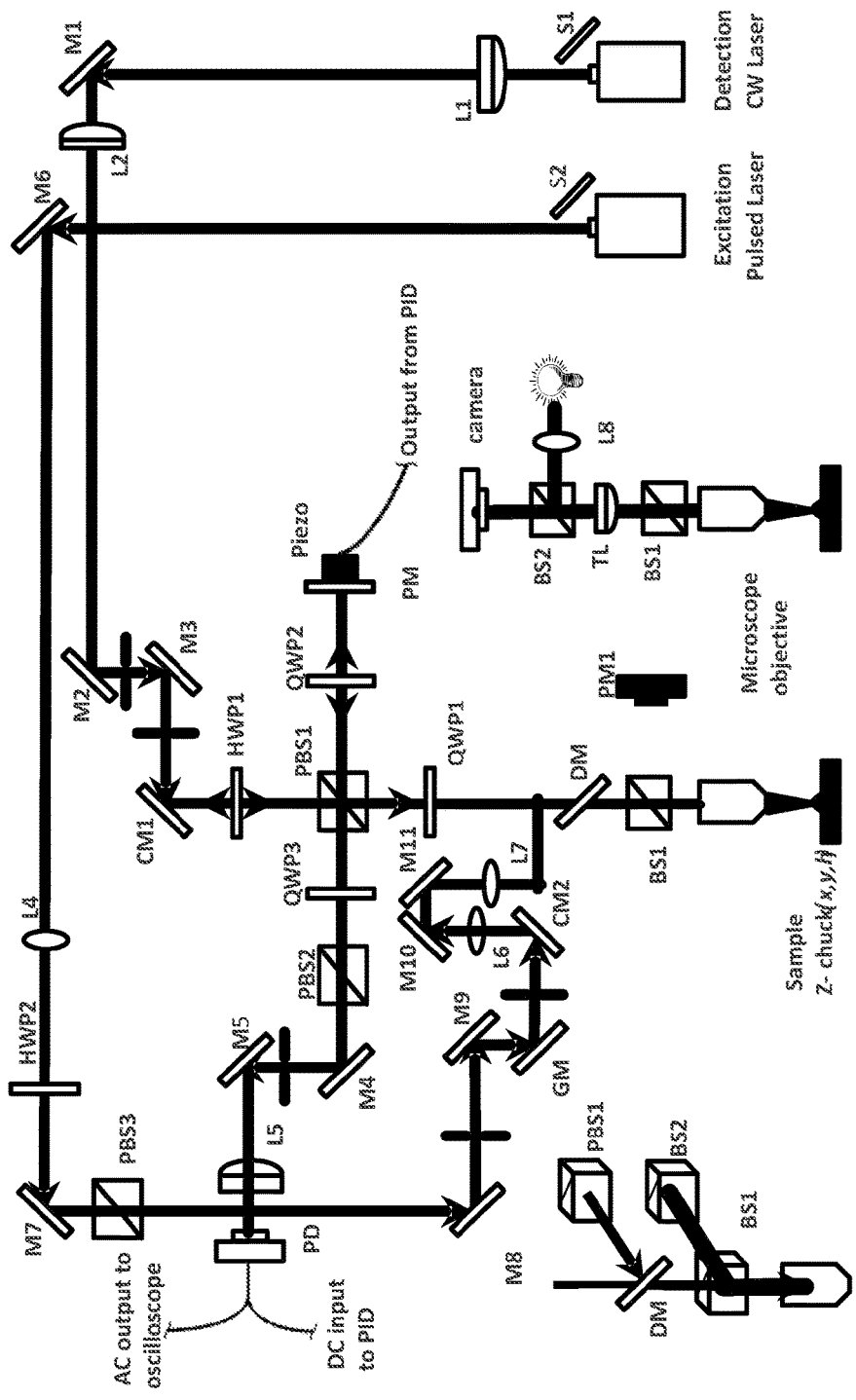
FIG. 2 depicts another example of a system suitable for performing void detection through opto-acoustic metrology.

FIG. 2 depicts another example of a system suitable for performing void detection through opto-acoustic metrology. In the depicted embodiment an excitation pulsed laser directs a laser beam through a series of mirrors M6, M7, M8, M9, GM, CM2, M10, M11 and lenses L4, L6, L7 and other optical components a half wave plate HWP2, a polarizing beamsplitter PBS3, a non-polarizing beamsplitter BS1 to the sample located on the chuck. The excitation laser beam can alternatively be directed through lens L5, mirrors M5, M4, and a polarizing beam splitter PBS2 and a quarter wave plate QWP3. A detection laser directs a laser beam to through a series of mirrors M1, M2, M3, CM1 and lenses L2 and other optical components a half wave plate HWP1, a polarizing beamsplitter PBS1, a quarter wave plate QWP1, a dichroic mirror DM, and a non-polarizing beamsplitter BS1 to the sample located on the chuck. In the depicted embodiment, the system further includes a subsystem including a dichroic mirror DM a polarizing beam splitter PBS1, a nonpolarizing beamsplitter BS1, and a non-polarizing beamsplitter BS2 and a subsystem including a camera, a non-polarizing beamsplitter BS2, lense L8, tube lense TL, a nonpolarizing beamsplitter BS1. Those having skill in the art will appreciate variations of the systems depicted in FIGS. 1 and 2 that would still be suitable to carry out the opto-acoustic metrology techniques described herein.

In some examples, a short excitation laser pulse at 532 nm wavelength is directed towards a sample, where it is partially absorbed at the sample surface and generates broadband acoustic waves that propagate through the TSV. In such an example, the pulse duration of the excitation laser is ~300 psec. An optical interferometer with a CW probe laser at 660 nm is used to monitor the displacement of the TSV surface following the laser excitation. Such an example provides the flexibility to move the excitation and probe beams such that the two beams may be overlapping or separated, depending on the application of interest. For detection of voids in TSV structures, both beams are generally overlapping and centered over the via. The excitation laser spot is typically set to a diameter larger than the via to facilitate effective excitation of acoustic modes, while the probe laser is focused to ~3 µm diameter.

Figure 3:
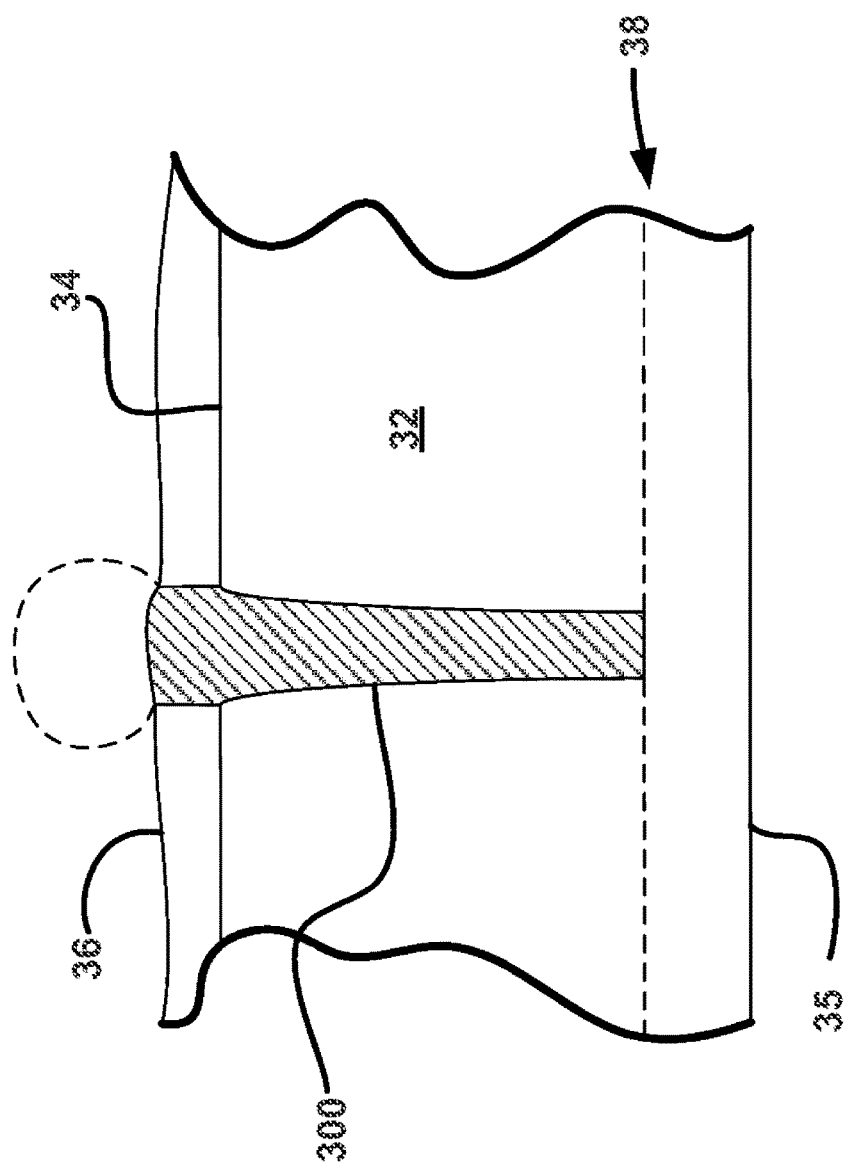
FIG. 3 illustrates an example of a through silicon via.

The sample may be a silicon wafer having a TSV. FIG. 3 illustrates an example of a TSV 300. Those skilled in the art will readily understand that this type of via is representational only and that the present invention may be applied to many different types of via. It is noted that a given substrate may have one or more than one structure such as the illustrated via 300, and in some instances may have many thousands of such structures.

Via 300 is formed through an upper surface 34 and into the body of a substrate 32, in this case a silicon semiconductor substrate. Conductors and/or insulators that form the active portion 36 of an integrated circuit device are deposited onto the upper surface 34 of the substrate 32. Note that the active portion 36 may itself be formed of multiple discrete layers (not shown) using any one of a number of known lithographic techniques including, but not limited to, etching, deposition, masking, and develop. In some instances the upper, exposed surface of the via 300 will be used to form connections to other structures. This can be done by laying conductive traces (not shown) over the upper, exposed surface of the via 300 or, as shown, placing a solder bump or pillar in contact with the via 300. Note that in general, but not in all cases, bumps/pillars or other connections will be made at a stage in the fabrication process that is later than when the inspection techniques of the present invention are employed.

In the example shown in FIG. 3 via 300 terminates within the body of the substrate 32. Dashed line 38 indicates the position to which the substrate 32 will be ground or removed, thereby exposing the bottom surface of the via 300 for connection to other structures or integrated circuits. The systems and methods disclosed herein can be used in the microchip fabrication process. For example, prior to back grinding a wafer, the via can be inspected for void. If the metrology step identifies that a void exists in the via that renders the via defective, the costly and timely step of back grinding can be avoided. Therefore, according to one method of manufacturing, the back grinding occurs only if the via inspected is determined not to include voids that would render the via defective. The system and method can also be integrated into the fabrication process as a control to monitor production and aid in the upstream setup of processes. In other words, the system and method can be used to inspect structures such as vias to identify when the processes used to form the via have developed a problem as certain types of small voids are noticed or other unusual and undesirable structural changes begin to occur within the vias. Inspection of vias 300 and other 3D structures in a substrate 32 is a difficult proposition. Much of the active portion 36 of a substrate is opaque to optical imaging techniques. Some techniques utilize near infrared illumination and imaging techniques to view vias 300 from the reverse side 35 of the substrate 32. Infrared imaging techniques are, however, subject to certain resolution and noise problems. The use of surface acoustic waves that travel in the active portion 36 of the substrate 32 or in the region of the substrate immediately adjacent the upper surface 34 of the substrate 32 avoids many of the drawbacks associated with imaging vias 300 and other structures.

As the systems and methods of the present disclosure are used to determine and identify characteristics of structures, such as vias, of a substrate on a repeated basis, it is desirable for the controller to record a series of instructions for the operation of the present invention that permit for easy automation of the process. Such lists of instructions are often referred to as a "recipe." A recipe may be a list of text or binary inputs that may be read and implemented by the controller to carry out the determination of substrate characteristics. The recipe may include not only simple instructions, but also generic information about the substrates that allow the controller to perform as intended. Examples of data that may be included in the substrate are the size and shape of structures as well as the location of sub-units of the substrate, e.g., the location of semiconductor devices on a wafer. The recipe may also provide for controlling and measuring data regarding the chemical, mechanical, and/or electrical processes used to generate the various structures. Further, the recipe may include the nominal locations of all structures found on a substrate or a subset thereof. As will be appreciated, the recipe may provide for controlling, lithography systems (steppers/scanners), coaters, bake or curing ovens, developers, washing/cleaning systems, metrology systems, inspection systems, amongst other tools utilized in generating a final product. At each step in the recipe, data may be captured relating to dwell times, temperatures, power flows (e.g. plasma etch systems or chemical vapor deposition systems), chemical concentrations, electrical testing data, optical inspection data, and metrology data, among other types of data. The captured data may synthesized to identify correlations between the characteristics identified during metrology/inspection data and the process data. Based on the correlations the recipe may be modified to make subsequent IC chips based on metrology/inspection results.

In one example, the controller directs the stage to position the substrate such that radiation beams may be incident upon a desired point, such as a via. In this embodiment, the substrate is moved in a stop/start fashion, serially positioning the substrate in a desired location and then dwelling at that location long enough for extraneous vibration to be damped out, for optical elements to be focused at the desired point, and for data concerning characteristics of the structures to be captured. Multiple data gathering cycles may be undertaken during each stationary period in this manner.

In another example, the controller directs the stage to move continuously so as to continually shift the points of incidence past the incident radiation beams. Where the continuous movement of the substrate is sufficiently slow as compared to the pump/probe data collection process, one may consider each data gathering cycle (each pump/probe cycle) to have been conducted at an individual spot whose location is the center of the path that has been scanned during any given period. In this embodiment, multiple if not all vias on a substrate may be scanned. Often this is done by establishing a boustrophedon path that sequentially brings all structures that are to be scanned to their desired location. Following a path of this type allows for rapid assessment of the substrate. In other embodiments, the boustrophedon path is used, but rather than inspecting or assessing all structures, only selected ones are addressed. In yet another embodiment, the stage moves the substrate along a path fit to the location of selected vias on the substrate. This path may be a spline or a combination of linear and arcuate path sections.

In another example, the optical system which carries out the pump/probe data gathering cycle is provided with optical mechanisms that allow the pump and/or probe beams incident upon the desired points to be moved rapidly, i.e., dithered, to avoid imparting too much heat to any given location. In this case, one will consider the desired point to be the center of a region over which the beams are dithered. Data generated and collected by this arrangement are assigned to the center location defined by the desired point. This dithering technique may be used regardless of whether the substrate and stage move continuously or discontinuously. In yet another embodiment, the optical mechanisms used for dithering a beam over a particular area or region of a substrate may be used to maintain a pump/probe beam on a desired point as the substrate is scanned past the source of the pump/probe beam.

If during the metrology/inspection phases of the recipe, voids or other imperfections are identified in one or more structures, the wafer containing the defects may be diverted from the production line. Such diversion may be controlled by a controller. In examples, a wafer is diverted if the wafer contains more than a predetermined threshold of imperfections. After being diverted, the wafer may be inspected more thoroughly to identify whether the entire wafer needs to be discarded in its entirety or whether only certain devices are affected. If only certain devices are affected, then a wafer map, which identifies each chip on the wafer, can be modified ensure chips or structures having imperfections are not used, while the chips or structures without imperfections are preserved for use.

Figure 4:
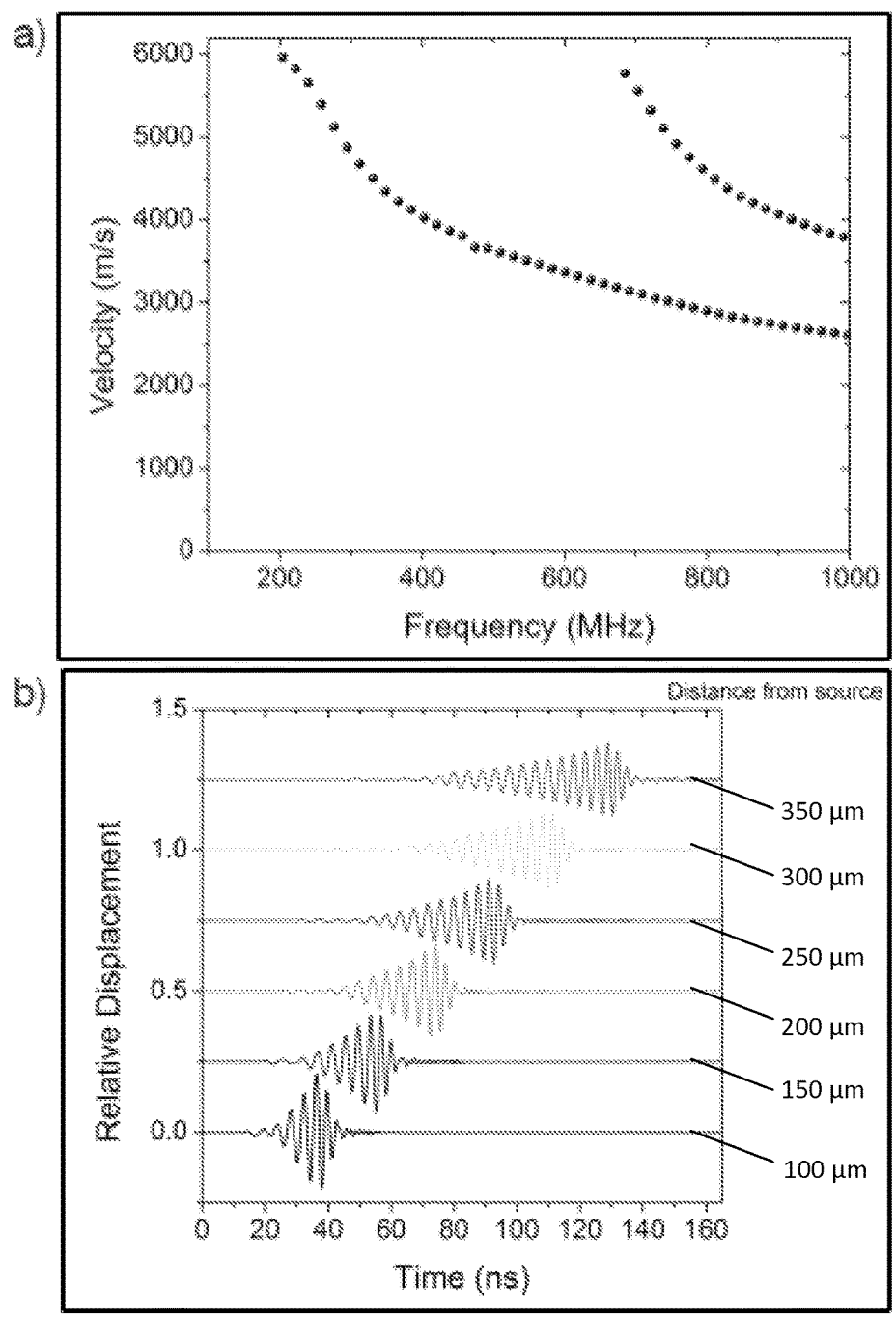
FIG. 4 illustrates sample material displacement normal to the TSV surface calculated as a function of propagation distance.

In TSV evaluation, an effective measurement strategy is to excite elastic waves with a laser source on the top of a copper filled TSV and detect the resulting TSV surface displacement as a function of time. A copper filled TSV acts as an elastic waveguide, and the propagation characteristics are governed by the reflection and refraction of waves at the copper and oxide/silicon boundary. Elastic waves propagating in such a cylindrical waveguide are dispersive, meaning that the phase velocity depends on frequency. In order to better understand wave propagation in TSV structures, a numerical model can be developed using explicit time domain, Finite Element Modeling (FEM), using the PZFLEX software offered by Weidlinger Associates in Mountain View, Calif. In a particular example, a 5 µm copper filled TSV surrounded by silicon may be considered. Laser heating of the free TSV surface produces rapid thermal expansion followed by a comparatively slow cooling. This physical process is simulated in the finite element model using a surface force dipole (for instance, with a 2 µm spot size) with a time dependence given by the integral of a Gaussian pulse (for instance, with a 3 ns pulse width). The rapid thermal expansion generates elastic waves which propagate through the TSV, and the material displacement normal to the TSV surface is calculated as a function of propagation distance. The results are given in the upper chart (a) in FIG. 4 for propagation distances between 100 and 350 µm. From these time domain responses, the dispersion curve, giving the explicit dependence of phase velocity on frequency, may be calculated and sample results are shown in the lower graph (b) in FIG. 4. Based on the results, it is found that the excitation source primarily generates a single mode in the TSV; the lowest order longitudinal mode. The second longitudinal mode is also generated, albeit with much smaller amplitude. The first mode shows strong dispersion, with the higher frequencies propagating significantly slower than the lower frequencies, which leads to the broadening of the wave packet with propagation distance observed in the simulation results.

The fact that elastic waves can be excited by a pulsed laser source and guided along TSV structures opens up the possibility of using them to probe high aspect ratio copper filled TSVs for the presence of defects. In particular, poorly filled TSV structures and/or the presence of voids within the copper fill will lead to scattering and attenuation of the guided elastic waves. In this approach, the guided wave is detected by monitoring the displacement at the TSV surface subsequent to laser excitation.

For a defect free via, such as the one depicted in FIG. 3, the generated wave will propagate through the TSV, reflect from the bottom of the TSV, and return to the sample surface where it is detected. The expected time domain response will depend on the TSV height, or total round trip propagation distance. In poorly filled TSV structures, on the other hand, the transmission of guided waves through TSVs will be suppressed through scattering of the waves at the interfaces associated with inhomogeneities within the structure. This, in turn, will lead to (a) a reduction in the amplitude of the guided waves reflected from the bottom of the TSV and (b) the arrival of scattered acoustic waves in the time window before waves are expected from the bottom of the via. In addition, the waves reflected from inhomogeneities in the TSV will have a different temporal signature than those from the TSV bottom due to the different propagation distance and dispersive nature of the wave propagation. The net result is that the laser induced acoustic response allows for a clear distinction between filled and poorly-filled TSV structures.

Figure 5A:
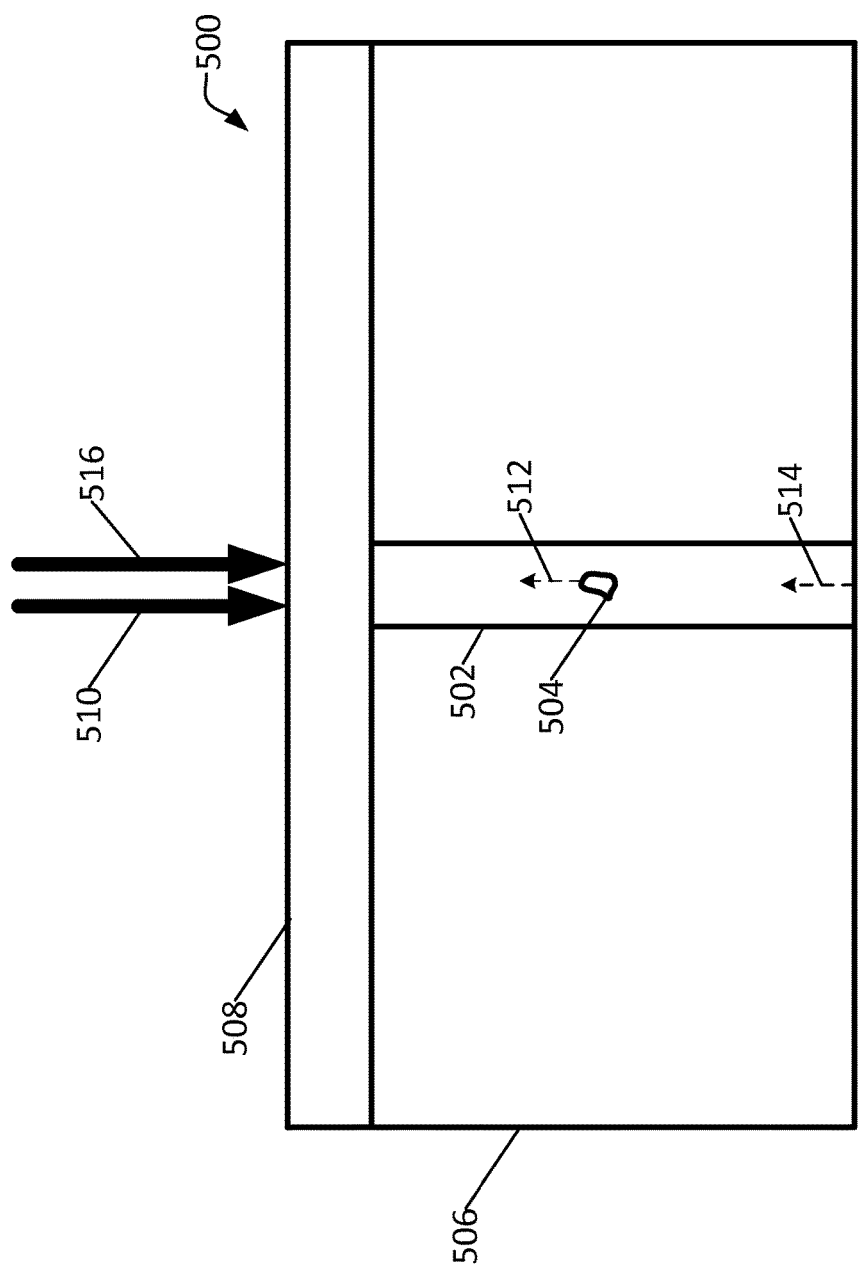
FIG. 5A depicts a sample having a via with a void within the body of the via.
Figure 5B:
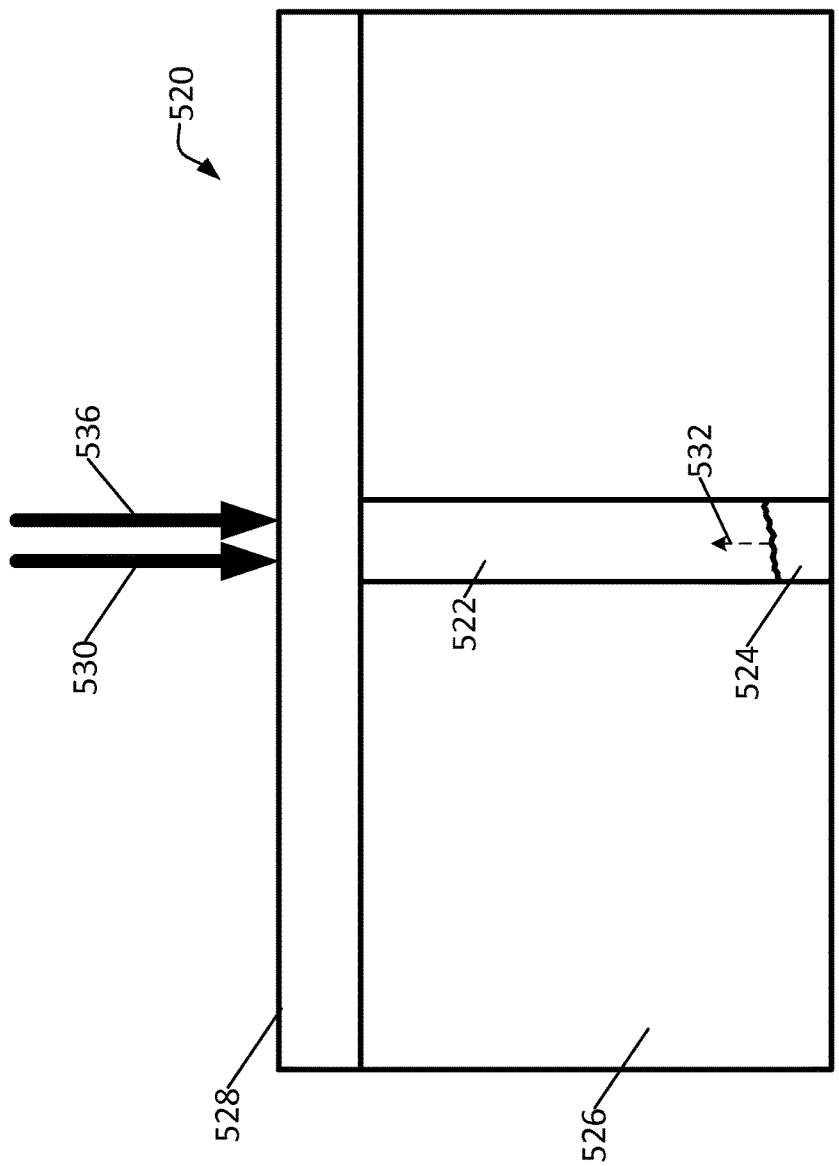
FIG. 5B depicts a sample having a via with a void in the bottom of the via.

FIGS. 5A and 5B illustrate two types of poorly filled vias of interest. FIG. 5A depicts sample 500 having a via 502 with a void 504 within the body of the via 502. In examples, the via 502 may be encased in a silicon layer 506 having an upper silicon-oxide surface layer 508. As shown in FIG. 5A, an excitation laser emits an excitation beam 510 directed towards the via 502 that causes an acoustic wave to propagate through the via. Due the void 504 in the via 502, the acoustic wave reflects off the void 504, as shown by the void reflection 512. The acoustic wave will also reflect from the bottom of the via 502, as shown by the bottom reflection 514. The reflected waves are then detected by the probe beam 516. While the probe beam 516 and the excitation beam 510 are depicted as being adjacent to one another in FIG. 5A, in examples, the probe beam 516 and excitation beam 510 would be concentrically focused to approximately the same location on the sample 500.

FIG. 5B depicts a sample 520 having a via 522 that has been incompletely filled, creating a bottom void 524. In examples, the via 502 may be encased in a silicon layer 526 having an upper silicon-oxide surface layer 528. As shown in FIG. 5B, an excitation laser emits an excitation beam 530 directed towards the via 522 that causes an acoustic wave to propagate through the via. Due the bottom void 524 in the via 522, the acoustic wave reflects off the bottom void 524, as shown by the void reflection 532. The reflected wave 532 may also disperse depending on the shape of the void. The reflected wave is then detected by the probe beam 536. While the probe beam 536 and the excitation beam 530 are depicted as being adjacent to one another in FIG. 5A, in examples, the probe beam 536 and excitation beam 530 would be concentrically focused to approximately the same location on the sample 520.

Figure 6A:
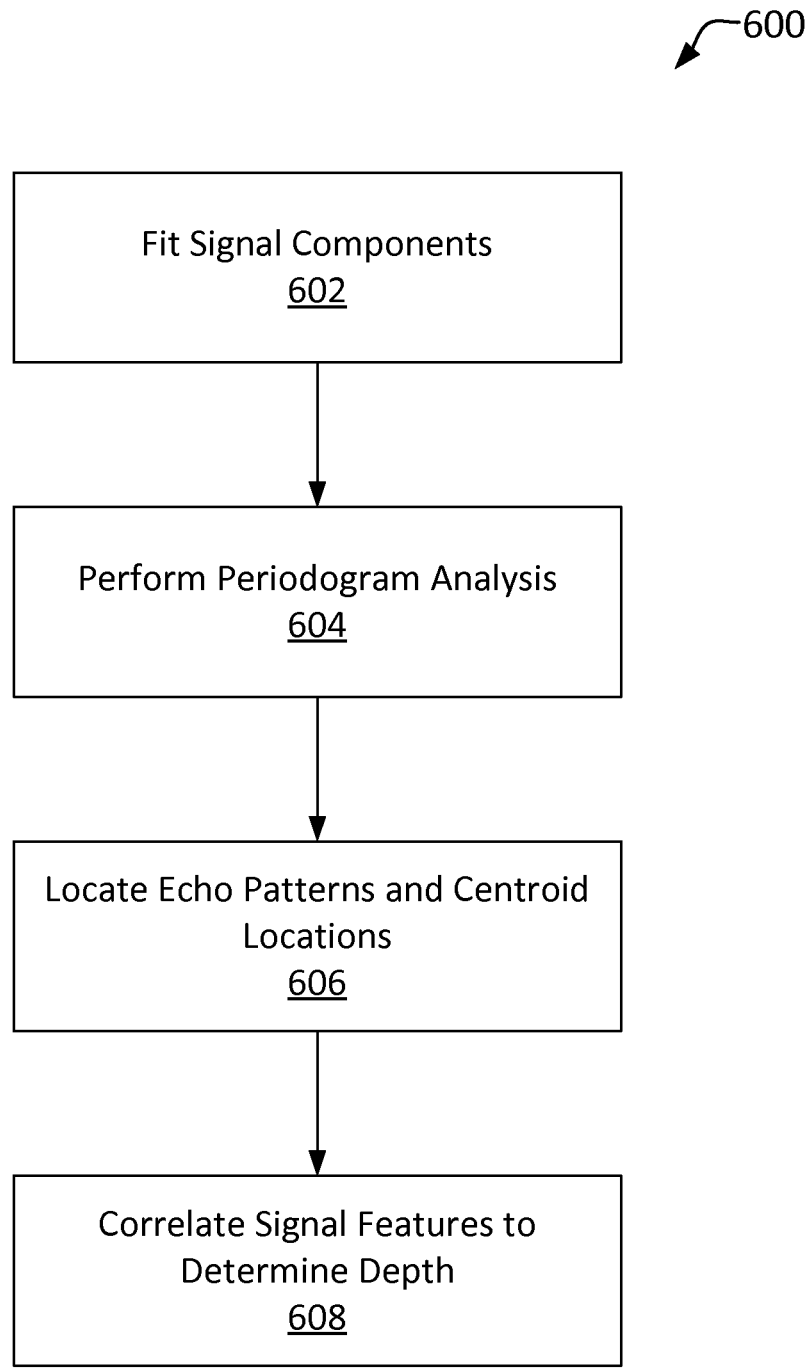
FIG. 6A depicts an example of a method that can be used to generate a model to detect voids and the position of those voids in a via.

Opto-acoustic metrology to detect voids in vias, such as those shown above in FIGS. 5A and 5B, can be accomplished based on the following considerations and operations. FIG. 6A depicts an example of a method 600 that can be used to generate a model to detect voids and the position of those voids in a via. In method 600, the signals analyzed may be signals generated from a computer model or test signals received by performing the optical-metrology techniques discussed above on a predetermined sample. At operation 602, the model and/or test signal components are fitted. For example, operation 602 may include fitting the slow signal component due to temperature rise and subsequent heat dissipation with a polynomial and subtracting it to isolate acoustic component of the signal. The slow signal component due to temperature rise and subsequent heat dissipation has a lower frequency than that of the acoustic component of the signal. Operation 602 is performed because as the excitation pulse is absorbed, the sample is rapidly heated and undergoes thermo elastic expansion. Detection of the material displacement contains two major contributions: a slow decaying component due to the heat dissipation away from the area where the excitation pulse energy was absorbed, and a higher frequency oscillatory acoustic component. The low frequency does not contain information relating to the subsurface structure of the via. Therefore, the first step of the data processing algorithm subtracts the slower background component by fitting it with the polynomial.

At operation 604, a model periodogram analysis is performed on the acoustic component of the model and/or test signal. In performing the model periodogram analysis, a sliding window with a width comparable to the time width of the echo pulse (~10 ns) may be run over the data, and the Fourier transform of this windowed signal is calculated. A Hann window with the time width of a few nanoseconds, commensurate with the time duration of the generated acoustic pulse may be used. The periodogram signal is defined as the time dependent amplitude of the Fourier transformed time windowed signal, $P(t,\mu)=|FT(t,\mu)|$. More specifically, periodogram $P(\mu,f)=|FT[u(t),\mu)]|$, is defined as amplitude of the Fourier transform of the top displacement $u(t)$ signal, detected by the probe pulse, calculated with the window centered at delay time $\tau$.

Based on the periodogram analysis performed in operation 604, further analysis is performed at operation 606 to extract the returning echo features, and their characteristics e.g. centroid time and frequency, time and frequency width, etc. For instance, modified image processing segmentation algorithms may be used to locate the echo patterns, and find their model centroid locations $(\tau,f)$. These values can then be used to correlate to the location and size of defects in the via at operation 608. Correlations can be established using FEM simulations, from real samples that have been analyzed using FIB SEM, or using other techniques. The echo centroids and amplitude may be utilized in order to identify the presence of the voids inside the bulk of the via, such as depicted in FIG. 5A, and those associated with a defect at the via bottom, such as depicted in FIG. 5B.

To determine the correlative properties used to determine the location of the via defects, an FEM model can be used to simulate the temporal and spatial evolution of the temperature rise due to the excitation pulse energy being absorbed. The thermal results may then be coupled into the mechanical model to simulate elastic wave propagation within the sample. The vertical displacement at the top surface in the via center may then be recorded to mimic the particular systematic setup being used.

Figure 6B:
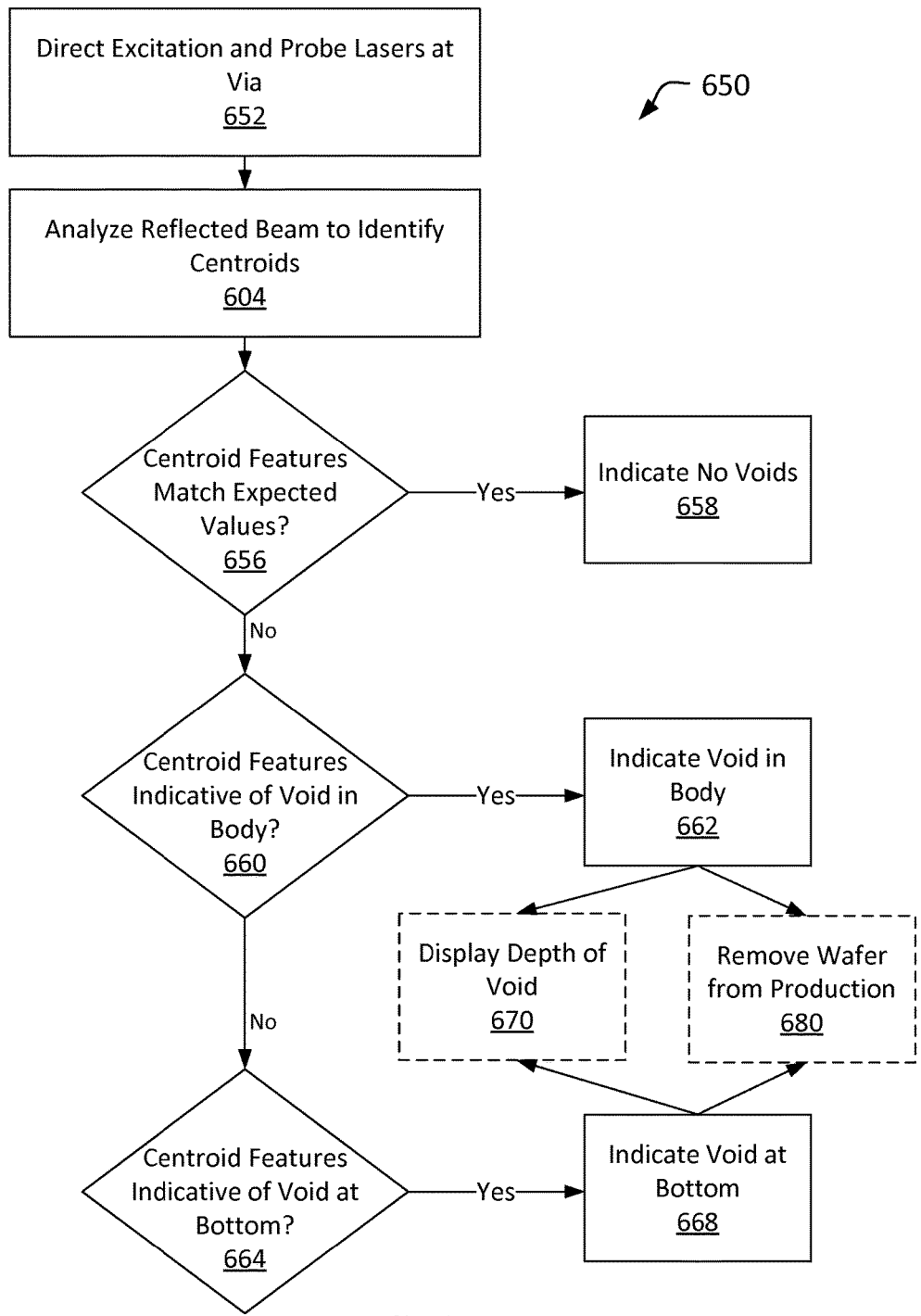
FIG. 6B depicts an example of a method for determining the existence and location of voids in a via.

FIG. 6B depicts an example of a method 650 for using the analysis performed in method 600 to determine the existence and location of voids in a via. At operation 652, an excitation laser beam and a probe laser beam are directed towards the via. As discussed above, the excitation laser beam causes an acoustic wave to propagate through the via. The probe beam reflects off the sample and the resultant reflected beam encodes data about the propagation of the acoustic wave, as also discussed above. At operation 654, the reflected beam is detected and the detected reflected beam is analyzed to identify centroids. Analyzing the reflected beam involves substantially the same operations as those in method 600 depicted in FIG. 6A. For example, the signal components of the reflected beam may be fitted to remove the background signal, similar to operation 602. The detection periodogram may also be created by performing a periodogram analysis on the reflected wave, similar to operation 604. From the detection peridogram, the echo patterns and detection centroid locations also may be determined, similar to operation 606. In identifying the detection centroid locations, the features defining the location, such as the frequency and the delay time associated with each respective detection centroid may be determined.

Once the detection centroid locations are identified and the features, such as associated delay time and frequency are determined, the features can be compared to the expected values determined through modeling or through performing method 600, discussed above. For instance, at operation 656 it is determined whether the detected features match the expected values for the features. In examples, the expected delay time is the delay time for a properly filled via and the expected frequency is the frequency for a properly filled via. In operation 656, the detected delay time may be compared to the expected delay time to see if they are substantially the same. If the delay times are substantially the same, and the detected frequency is approximately equal to the expected frequency, it is determined that the via has no voids and an indication is generated at operation 658 that the via has no voids. The indication may be displayed via LED indicators or through a display screen, or through other technology as will be appreciated by those having skill in the art. If, however, the detected centroid features do not match the expected values, it is determined that there is a void in the via and the process flows to operation 660 to determine if the centroid features are indicative of a void in the body.

In operation 660, the detection centroid features are further analyzed to determine if the detection centroid features are indicative of a void in the body of the via. In examples where two or more centroids are identified, centroid features are indicative of a void in the body of the via when an associated delay time of a first detection centroid is shorter than the expected delay time, and an associated delay time of a second detection centroid is approximately equal to the expected delay time. In conjunction with those delay time relationships, if the associated frequencies of the first and second detection centroids are substantially the same and approximately equal to the expected frequency, it is further indicative that the void is in the body of the void. If the centroid features do correspond to such relationships, an indication is generated that there is a void in the body of the via at operation 662. If the centroid features do not correspond to such relationships, the process flows to operation 664 to determine if the detection centroid features are indicative of a void in the body.

In operation 664, the detection centroid features are further analyzed to determine if the detection centroid features are indicative of a void in the bottom of the via. In examples where two or more centroids are identified, centroid features are indicative of a void in the bottom of the via when an associated delay time with a first detection centroid is shorter than the expected delay time and an associated delay time with a second detection centroid is approximately double the delay time associated with the first detection centroid. In conjunction with those delay time relationships, if the associated frequencies of the first and second detection centroids are substantially, it is further indicative that the void is in the body of the void. As another indicator, if there is a third centroid having a higher frequency than the first two centroids and a delay time between the delay times of the first two detection centroids, it is indicative of the void being at the bottom of the via. If the detection centroid features are indicative of a void at the bottom of the via, an indication is generated that there is void at the bottom of the via.

If a void is detected either in the bottom of the via or in the body of the via, the depth of the void also may be calculated using the correlations determined in operation 608 in method 600. That depth may then be displayed in operation 670. In addition, if one or more voids are detected, the wafer containing the voids may be diverted from the standard production process at operation 680. The wafer may be diverted if the wafer contains more than a predetermined threshold amount of voids. Once diverted, the wafer may undergo additional inspection. In other examples, each via in the wafer may be inspected as part of the recipe if one or more voids are identified. The additional inspection and processing of the wafer may also be used to modify the operation of one or more of the process tools used in the manufacturing of the wafer to mitigate the identified imperfections or voids in future wafer production.

As an alternative or in conjunction with directly comparing the detection centroid features with the expected centroid feature values. The depth of the corresponding centroids may be calculated based on correlations determined in operation 608 in method 600, and the calculated depths may be compared to the expected depth of a fully filled via. While there are particular relationships highlighted above with respect to expected and detected centroid features, other relationships are also indicative of the existence of voids and their respective locations. The examples below further illustrate the above-identified relationships along with additional relationships that may be utilized in the void detection techniques described herein.

Figure 7:
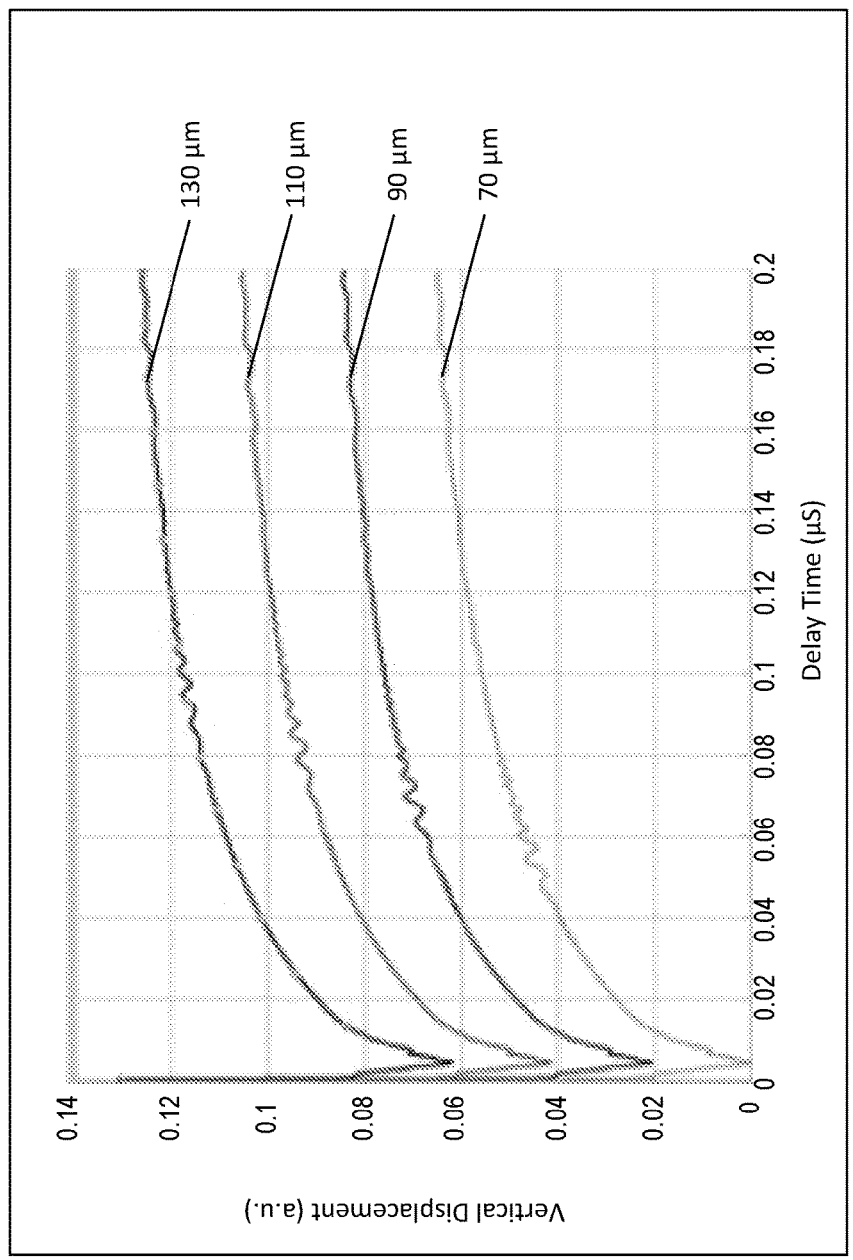
FIG. 7 displays the results of sample FEM analysis.

The following examples further explain and illustrate the methods and systems described above. One having skill in the art will recognize that the methods and systems above are applicable to more than the examples and experimental results discussed below. As one example, FEM analysis was performed by simulating Cu fill structures with overburden, and varying the depth of the via, and the results are shown in FIG. 7. The model in FIG. 7 depicts FEM Simulated signals for the defect-free filled Cu vias of 10 um diameter with 6 μm Cu overburden, varying via depth (70 μm, 90 μm, 110 μm, 130 μm). That model allows for the identification the major mode(s) excited during the laser-based acoustic measurements. Additionally, it allows a linear relationship between the arrival time of the reflected pulse and the via depth or the location of a defect that reflected the excitation pulse to be established. As shown in FIG. 7, the slowly rising component of the signal may be attributed to the slow component due to temperature rise and subsequent heat dissipation, while the ripple in each signal is attributed to the acoustic component of the signal.

A shift in echo position to later times is observed in FIG. 7 as via depth increases from 70 μm to 130 μm due to the pulse reflecting from the bottom of the via. As explained above, there is a guided wave coupling both shear and longitudinal components and its propagation speed is different from either shear or longitudinal sound velocities and may be strongly dispersive. Nevertheless, arrival time of the echo can be linearly correlated to the distance travelled by the pulse, with a good degree of accuracy. Via depth can be calculated by analyzing echo pulse that is reflected from the bottom of the via. Presence of voids inside the via would be characterized by additional reflections and their arrival times can be used to determine their location.

Figure 8:
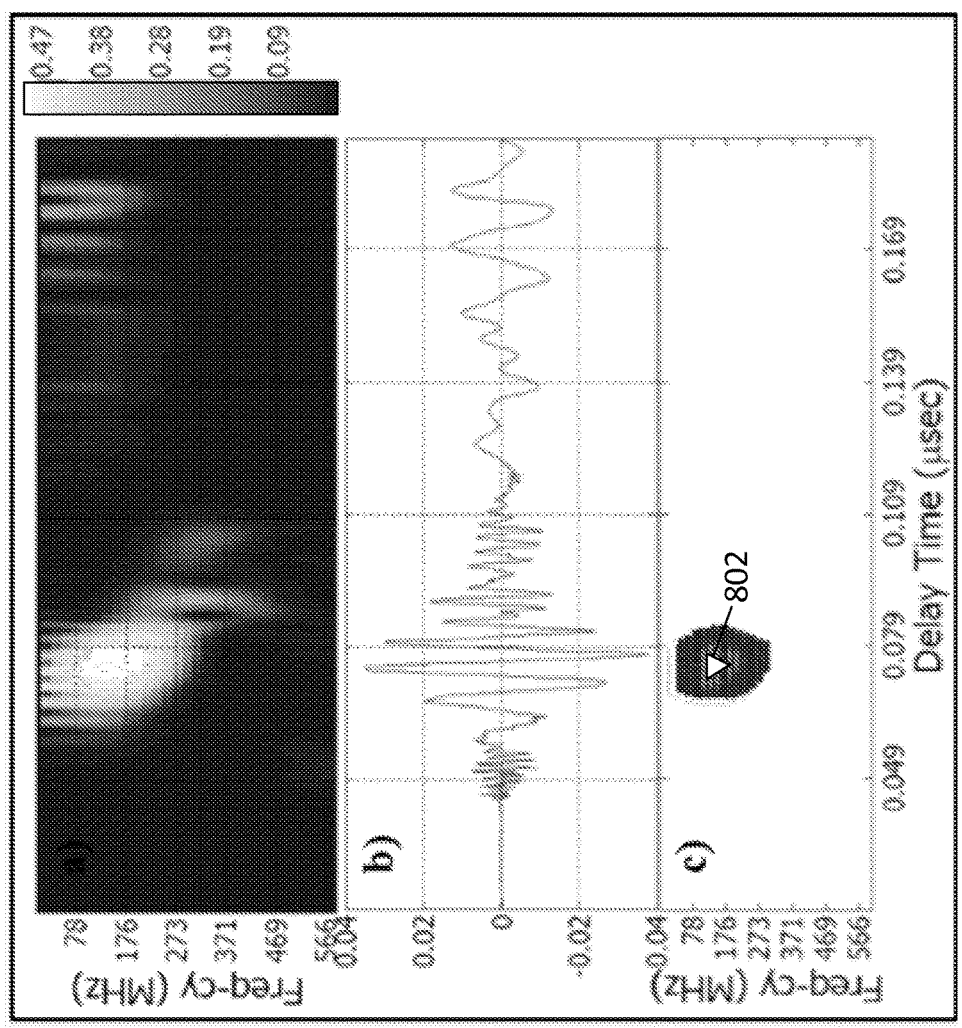
FIG. 8 shows FEM simulated results after signal processing for a 10 µm diameter, 100 µm deep via.

FIG. 8 shows the FEM simulated results after signal processing for a 10 μm diameter, 100 μm deep via. The upper portion of FIG. 8, marked with "a)", shows the periodogram. The middle portion of FIG. 8, marked with "b)", shows the background-subtracted signal, and the bottom portion, marked with "c)," shows the detected echo and centroid location 802. As can be seen from the data in FIG. 8, there is one reflection centroid generated in the simulation as there are no voids in the simulated via. The single centroid results from a simulated reflection of the acoustic wave from the bottom of the via.

The periodogram approach described above has been used for analyzing samples described in table below.

| Sample | Nominal (Diameter × Depth) | Copper Overburden |
|---|---|---|
| A | 10 μm × 100 μm | Yes |
| B | 10 μm × 100 μm | Yes |
| C | 5 μm × 50 μm | No. Post-planarization |
| D | 5 μm × 50 μm | No. Post-planarization |

These samples were selected as they show different signatures during the measurements and analyses and demonstrate the sensitivity of the technique to detect and characterize different types of voids at different depths. As seen from the samples listed in the table, the TSV samples have a 10:1 aspect ratio. The 5 μm×50 μm samples were measured after Chemical Mechanical Polishing (CMP).

Figure 9:
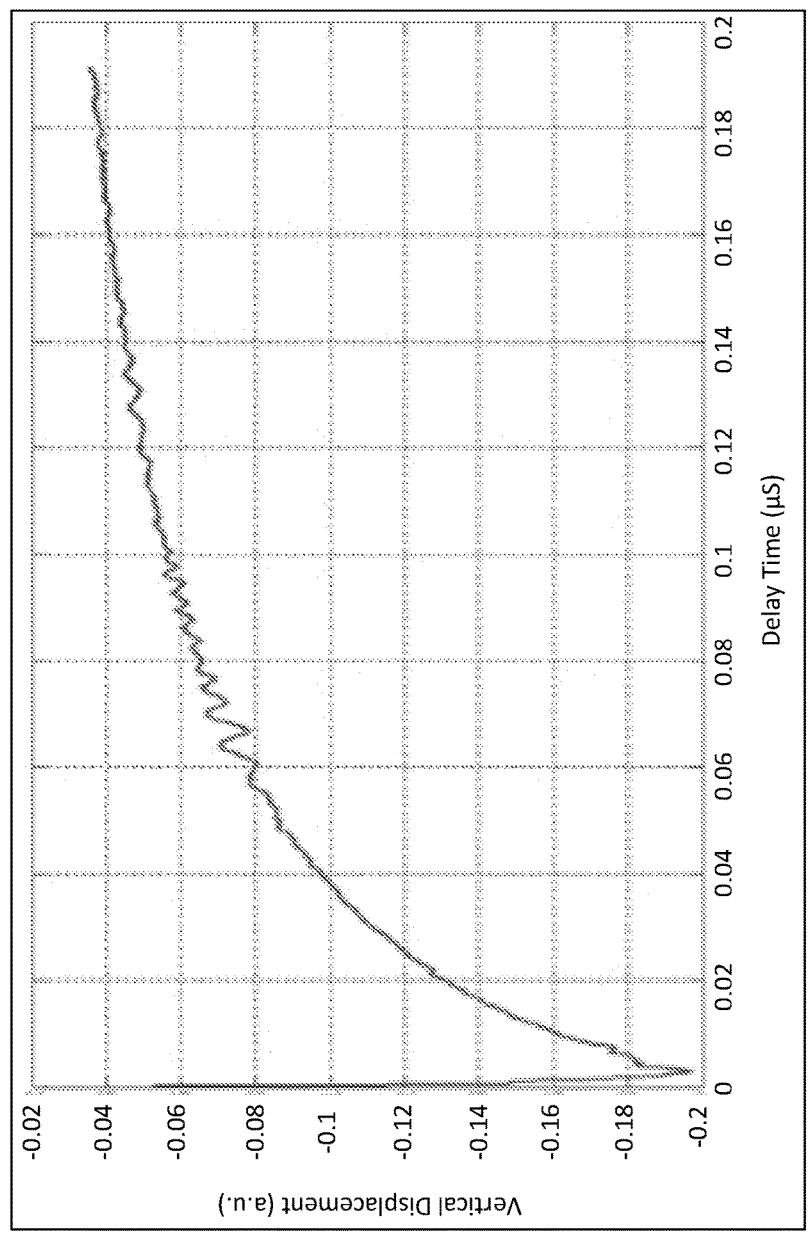
FIG. 9 shows the measurement signal as a function of delay time from a sample via.
Figure 10:
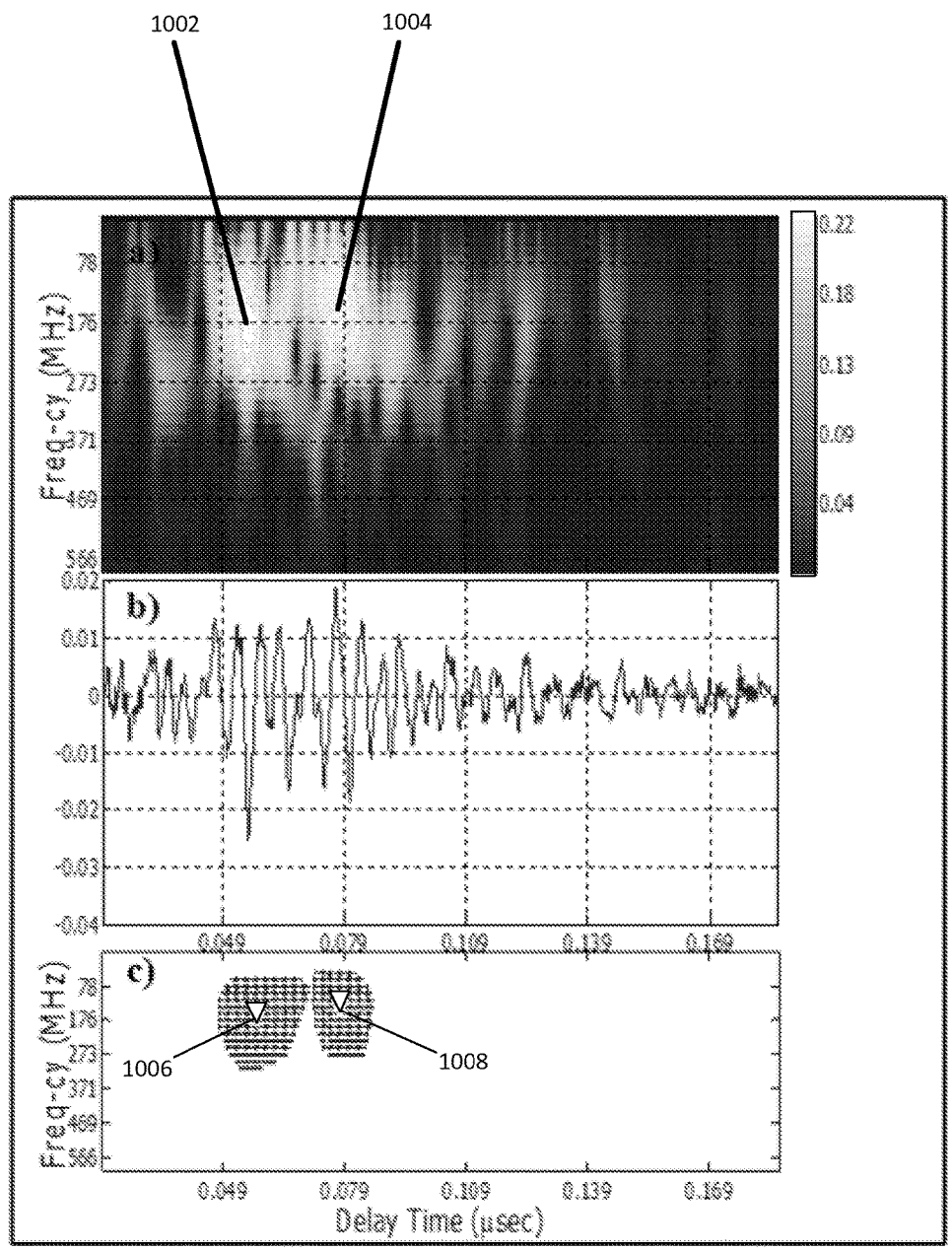
FIG. 10 shows an example periodogram, measured signal after scaling and background subtraction, and echoes with centroids.

FIG. 9 shows the measurement signal as a function of delay time from sample A. The via had a 10 μm diameter and was 100 μm deep. The measured signal after scaling and background subtraction is shown at the center of FIG. 10 and the corresponding periodogram at the top of FIG. 10. The shading scale of periodogram corresponds to the Fourier transform amplitude at a given time and frequency. Two bright features 1002, 1004 are observed in the signal. The second feature 1004 corresponds to the reflection from the via bottom (~0.075 μs) and an additional reflection (the first feature 1002) observed at ~0.052 μs is attributed to the presence of a void. Feature extraction analysis result, at the bottom of FIG. 10, shows the two echoes extracted with a first centroid 1006 at (0.054 μs, 170.6 MHz) and a second centroid 1008 (0.078 μs, 144.8 MHz).

Figure 11:
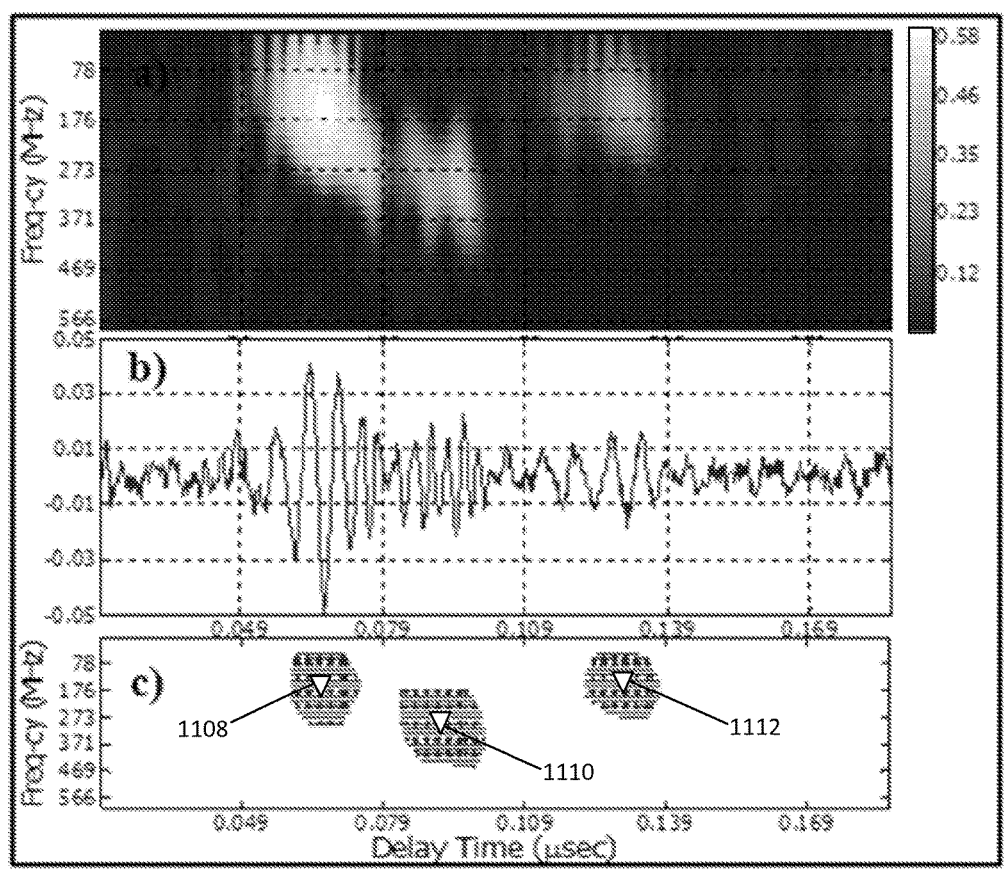
FIG. 11 shows an example periodogram, measured signal after scaling and background subtraction, and echoes with centroids.

FIG. 11 signal processed waveform along with the periodogram and feature correlation analysis is presented for sample B. The signature from this sample is representative of a large void present at the bottom of the via, such as the void depicted in FIG. 5B. When the large void occurs at the bottom of the via, the first reflection echo arrives earlier than expected from the via etch depth, and the second round trip at about double the delay time is also observed, as the acoustic contrast from the bottom void is much stronger, compared to the Cu/Si interface at the bottom of the properly filled via.

The 1st and 2nd round trip echoes are identified in FIG. 11 at centroid 1108 (0.066 μs, 143.8 MHz) and centroid 1112 (0.130 μs, 139.6 MHz), respectively. Following the same correlation, as before, this would correspond to the top of the void being located at 87.0 μm deep into the via. The centroid 1112 (0.130 μs, 139.6 MHz) echo corresponds to 183.0 μm distance traveled. This is close to twice the distance traveled by the first pulse, with the difference can be attributed to the guided mode dispersion.

Additional higher frequency echo found at centroid 1110 (~0.091 μs, 319.7 MHz), corresponds to a single pass reflection of the higher frequency pulse from the top of the void. Due to dispersion this higher frequency pulse would travel with a different speed, and thus follows a different correlation relationship between its delay time and distance traveled.

The measurement results shown in FIG. 11 were validated by performing FIB SEM analysis. The FIB SEM analysis showed the location of the void at ~89 μm, which is consistent with the measurement analysis above. Given the rough edges of the void, the slight discrepancy between the measurements and FIB SEM is to be expected. The sensitivity of the technique to detect voids in the bottom 12 μm of a 100 μm deep via, however, is a significant result. Detecting large voids present at the bottom of the via is useful as the large voids lead to no copper exposed when the wafer is thinned, preventing a good electrical connection to the redistribution layer (RDL) or solder bump.

In addition to the as-plated samples, described above, the present methodologies have also been tested on 5×50 μm vias post-CMP. One of the samples (Sample C) was processed such that the via was filled entirely, while the other sample (Sample D) was intentionally mis-processed so that a void was formed at the bottom of the via. The mis-processed sample (Sample D) was filled only to half the via depth, leaving the bottom of the via unfilled, similar to the via shown in FIG. 5B. Although the vias are nominally described as 5×50 μm, SEM imaging showed that the via length was only approximately 40 μm.

Figure 12:
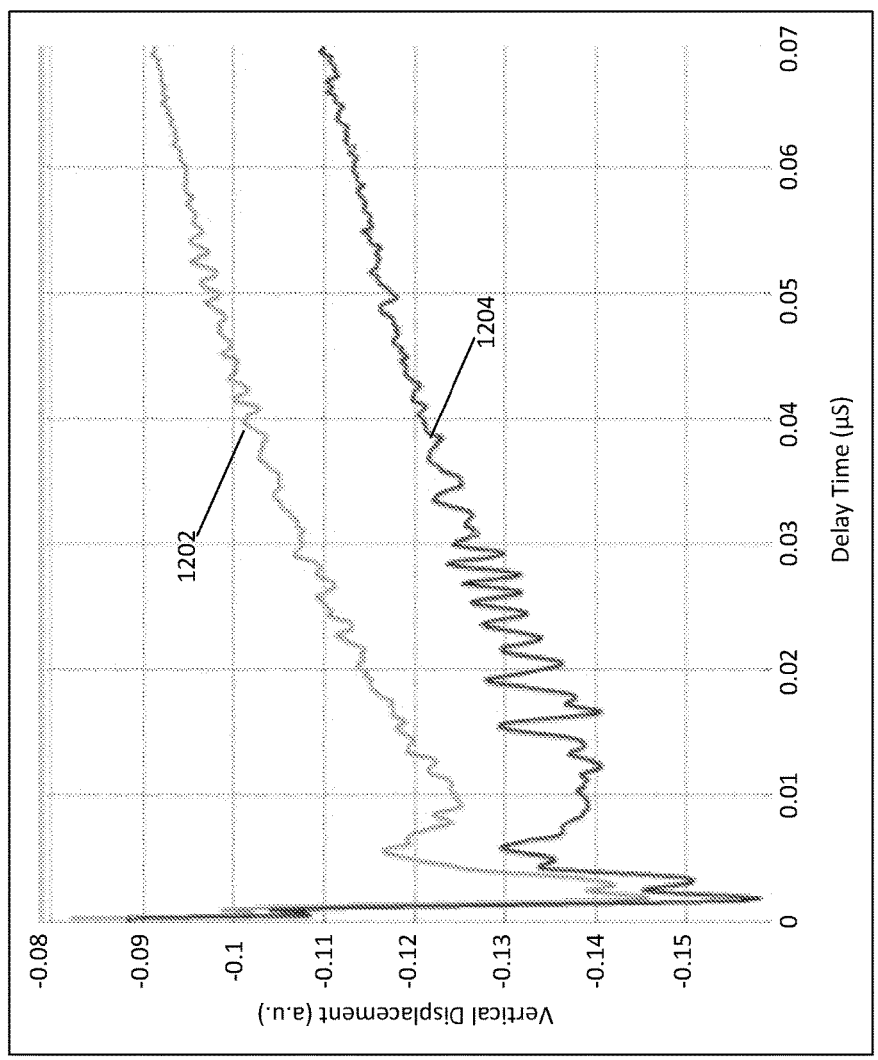
FIG. 12 shows measured signals from sample vias.

FIG. 12 shows measured signals from vias that were similar to Samples C and D. The fully filled sample measurement 1202 shows a reflected pulse delayed by approximately 0.030 μs indicating a good fill. On the other hand, a strong reflection echo is observed before 0.016 μs in the mis-processed sample measurement 1204 and is a manifestation of the via being only half-filled, to ~20 μm depth.

Figure 13:
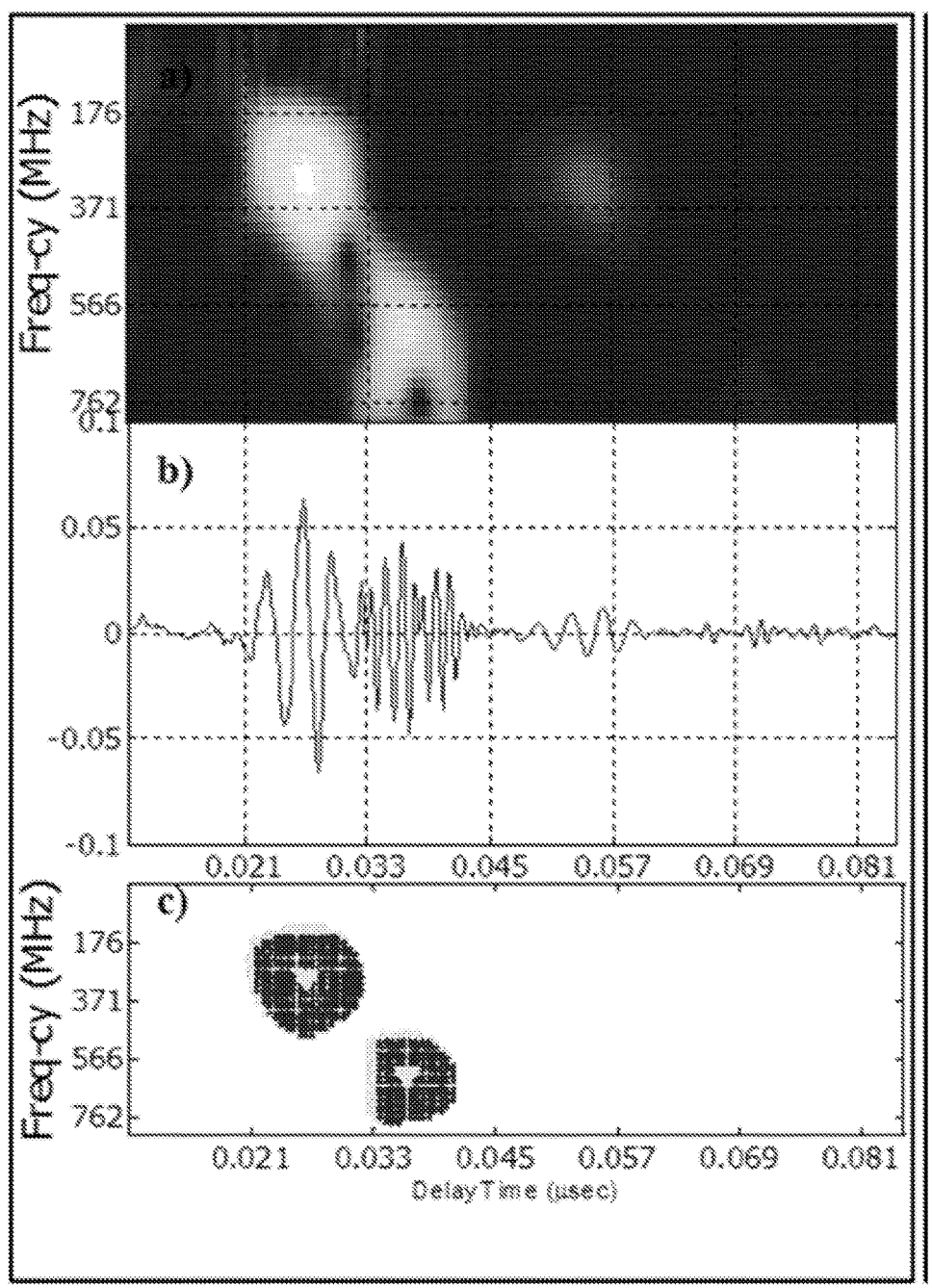
FIG. 13 shows an example periodogram, measured signal after scaling and background subtraction, and echoes with centroids.
Figure 14:
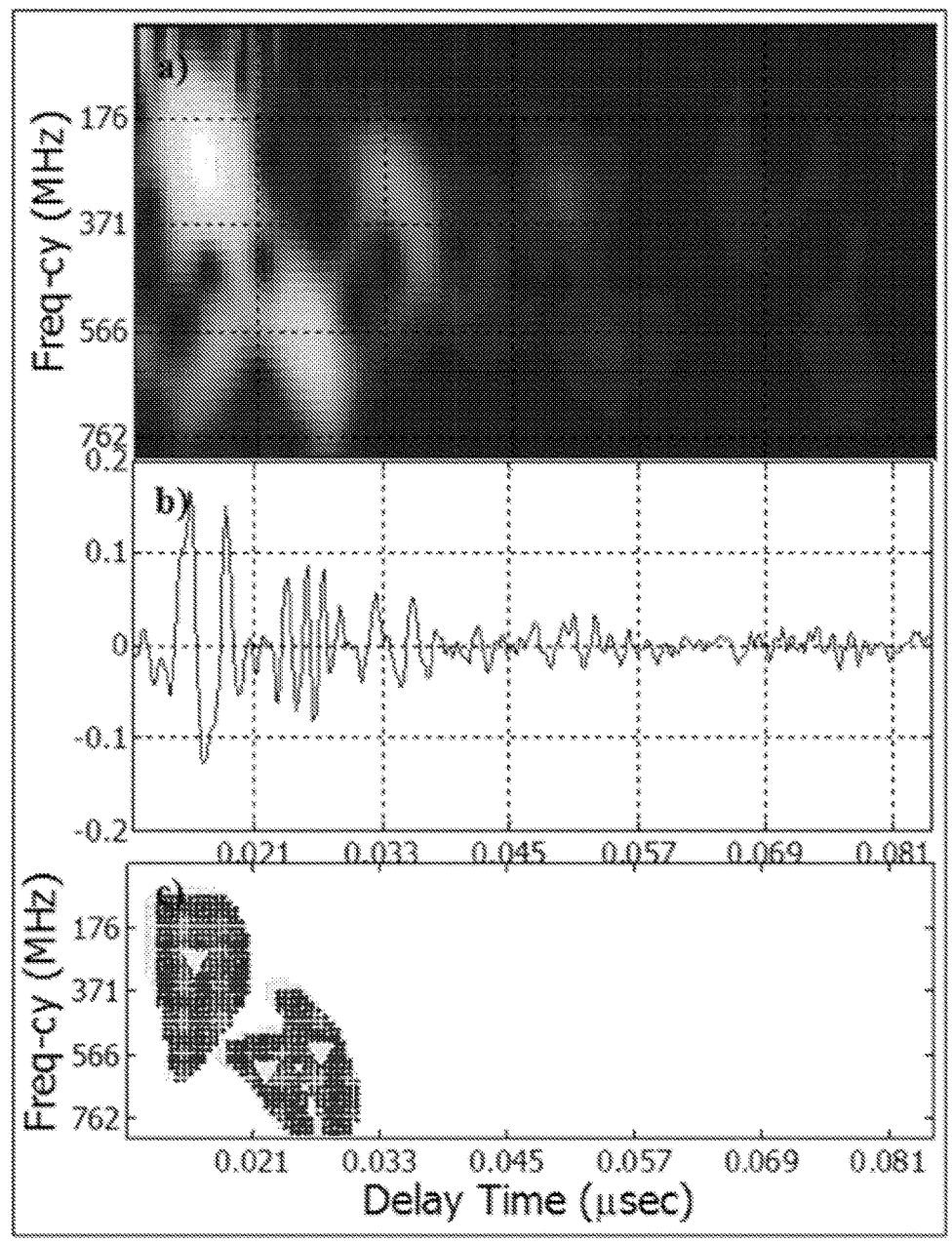
FIG. 14 shows an example periodogram, measured signal after scaling and background subtraction, and echoes with centroids.
Figure 15:
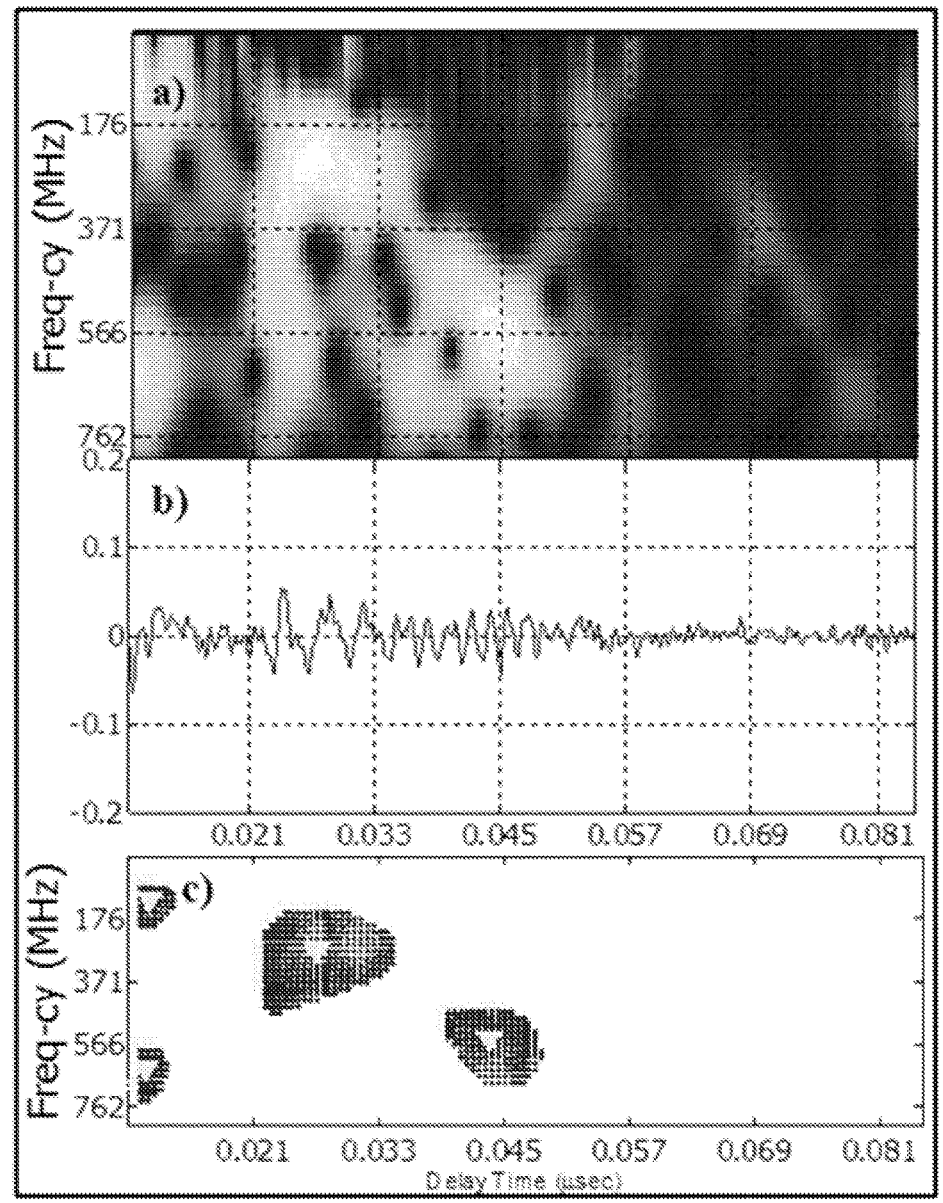
FIG. 15 shows an example periodogram, measured signal after scaling and background subtraction, and echoes with centroids.

FIG. 13 shows simulated data for the 40 μm deep via, while FIG. 14 and FIG. 15 show signals and echoes measured on the vias with and without voids, respectively. More specifically, FIG. 13 shows an FEM simulated signal from the post-CMP 5 μm diameter, 40 μm deep via. The echo at ~300 MHz is used to interpret the optoacoustic measurements. FIG. 14 shows the measured signal, periodogram, and identified echoes for the intentionally mis-processed sample (Sample D). FIG. 14 shoes the measured signal, periodogram, and identified echoes from the filled sample (Sample C).

Figure 16:
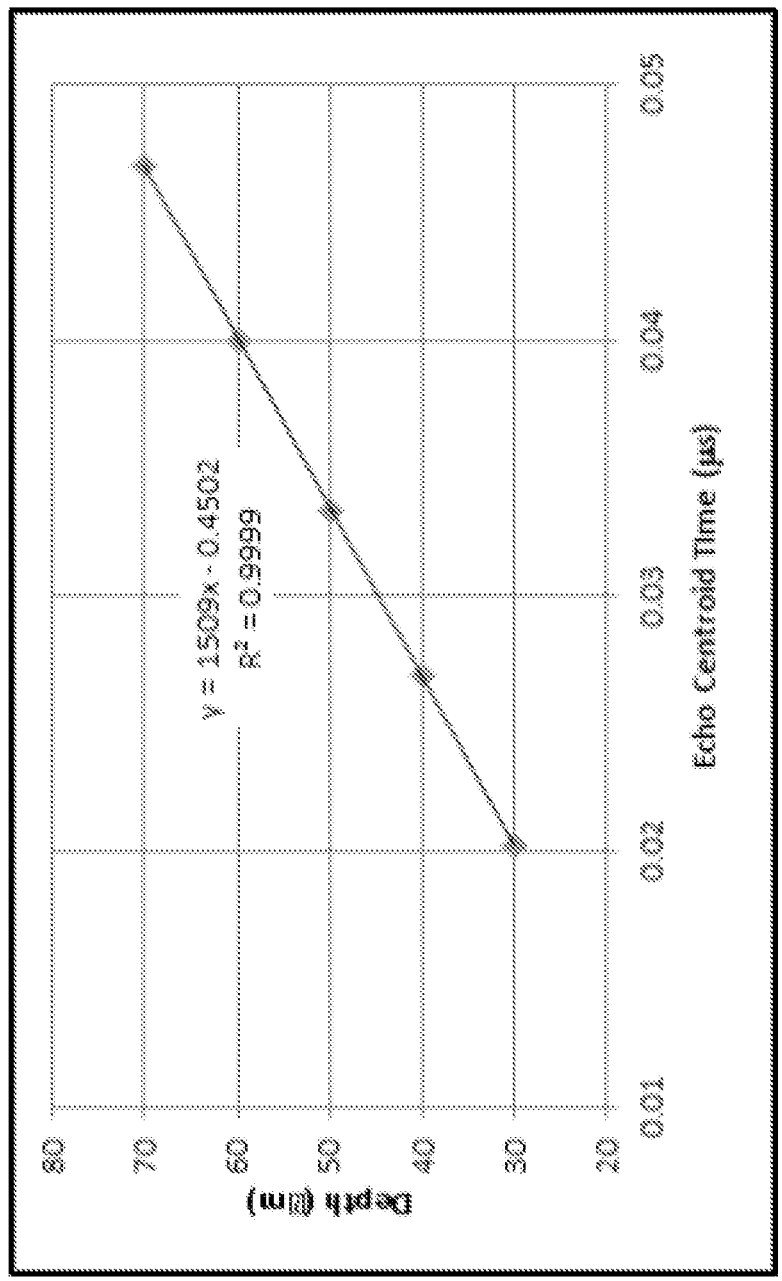
FIG. 16 shows a sample correlation plot.

Using a pulse frequency envelope around 300 MHz observed in both simulated and experimental data, the correlations can be established. In other embodiments, the experimental data or the experimental data may be used solely to determine the correlations. A sample correlation plot is shown in FIG. 16. The following correlation was obtained: $T(\mu m)=1509*t(\mu s)-0.45$. The results from Sample C (FIG. 15) shows the ~300 MHz echo centroid at 0.027 μs, corresponding to a depth of 40.58 μm, showing a strong correspondence to the actual depth measurement of approximately 40 μm. The mis-processed via signal from Sample D (shown in FIG. 14) has the echo pulse centroid at 0.015 μs, which corresponds to a copper depth of 23.0 μm inside the via, showing another strong correspondence to the measured depth of approximately 20 μm.

Accordingly, the present technology provides new and innovative techniques for the successful application of a laser-based ultrasonic method for the characterization of voids in TSV structures. This non-destructive method allows for full wafer sampling, process characterization and in-line control providing information on via depth, as well as location and depth at which the voids are present. The technique has been shown to be sensitive to different types of voids ranging from small conical voids that are a few μm wide to large voids that are buried in the bottom of 100 μm vias. Capability has been demonstrated on both as-plated and planarized samples. Typical measurement times are a few seconds per site and can be easily incorporated into in-line process monitoring. The technique may also be used for measuring copper pillar stacks, characterizing bonding voids and delamination.

The description and illustration of one or more examples provided in this application are not intended to limit or restrict the scope of the disclosure as claimed. For instance, while particular measurement values and representations have been used, it will be appreciated that these values are examples and are not meant to limit the scope of the claims to those particular values. The examples, embodiments, and details provided in this application are considered sufficient to convey possession and enable others to make and use the best mode of claimed disclosure. The claimed disclosure should not be construed as being limited to any embodiment, example, or detail provided in this application. Regardless of whether shown and described in combination or separately, the various features (both structural and methodological) are intended to be selectively included or omitted to produce an embodiment with a particular set of features. Having been provided with the description and illustration of the present application, one skilled in the art may envision variations, modifications, and alternate embodiments falling within the spirit of the broader aspects of the general inventive concept embodied in this application that do not depart from the broader scope of the claimed disclosure.

Unless otherwise indicated, all numbers expressing measurement properties, such as length, wavelength, depth, frequencies, and other similar properties used in the specification and claims are to be understood as being modified in all instances by the term "about" or "approximately." Accordingly, unless indicated to the contrary, the numerical parameters set forth in the following specification and attached claims are approximations that may vary depending upon the desired properties sought to be obtained. At the very least, and not as an attempt to limit the application of the doctrine of equivalents to the scope of the claims, each numerical parameter should at least be construed in the light of the number of reported significant digits and by applying ordinary rounding techniques.

The invention claimed is:

1. A method of non-destructive acoustic metrology for void detection in a via in a sample, the method comprising:
   generating a model for determining the existence of a void within the via, comprising:
      generating a model signal representative of a signal that would be received from performing acoustic metrology on the via;
      removing a signal component due to temperature rise and subsequent heat dissipation from the model signal;
      generating a model periodogram by performing a Fourier transform over a sliding window;
      applying a modified image processing segmentation algorithm to locate centroid locations of echo patterns in the model periodogram; and
      generating a correlation of the centroid locations to a depth of where a model acoustic pulse was reflected within the via; and
   directing an excitation laser beam at the via, such that an acoustic wave propagates through the via;
   directing a probe laser beam at the via, such that the probe laser beam reflects off the sample, creating a reflected beam encoding data about propagation of the acoustic wave in the via;
   analyzing the reflected beam, using a detection periodogram, to determine one or more detection centroids;
   applying the generated correlation to determine the depth of an acoustic wave reflection associated with the one or more detection centroids;
   comparing the determined depth with an expected depth for the via; and
   based on the comparison of the determined depth with the expected depth, generating an indication that there is the void in the via.

2. The method of claim 1, further comprising, based on the indication that there is a void in the via, diverting the sample from production for additional inspection.

3. The method of claim 1, wherein the model periodogram is represented as $P(\mu,f)=|FT[u(t),\mu)]|$ and is defined as an amplitude of a Fourier transform of a top displacement $u(t)$ signal calculated with a window centered at delay time $\tau$.

4. The method of claim 1, further comprising displaying the depth of the void in the via associated with a first detection centroid and a depth of the via.

5. The method of claim 1, further comprising determining whether the void is in a body of the via or at a bottom of the via.

6. The method of claim 5, wherein determining whether the void is in the body of the via or at a bottom of the via comprises identifying a first detection centroid having a first associated time shorter than an expected time and a second detection centroid having a second associated time of approximately double the first associated time.

7. The method of claim 6, wherein the first detection centroid has a first associated frequency and the second detection centroid has a second associated frequency, the first and second frequencies being approximately equal.

8. The method of claim 7, further comprising, based on the first and second associated times, determining the void is at the bottom of the via.

9. The method of claim 5, wherein determining whether the void is in the body of the via or at a bottom of the via comprises identifying a first detection centroid having a first associated time shorter than an expected time and a second detection centroid having a second associated time approximately equal to the expected time.

10. The method of claim 9, further comprising, based on the first and second associated times, determining that the void is in the body of the via.

11. The method of claim 5, wherein determining whether the void is in the body of the via or at a bottom of the via comprises:
   identifying a first detection centroid having a first associated time shorter than an expected time and a first associated frequency approximately equal to an expected frequency; and
   identifying a second detection centroid having a second associated frequency higher than the first associated frequency.

12. The method of claim 11, further comprising, based on the first and second associated frequencies, determining that the void is at the bottom of the via.

13. A method of non-destructive acoustic metrology for void detection in a via in a sample, the method comprising:
   directing an excitation laser beam at the via, such that an acoustic wave propagates through the via;
   directing a probe laser beam at the via, such that the probe laser beam reflects off the sample, creating a reflected beam encoding data about propagation of the acoustic wave in the via;
   analyzing the reflected beam, using a periodogram, to identify a first centroid and a second centroid, wherein the first centroid has a first associated delay time and a first associated frequency and the second centroid has a second associated delay time and a second associated frequency;
   comparing the first and second associated delay times to an expected delay time for an ideally filled via;
   comparing the first and second associated frequencies to an expected frequency range;
   based on the comparison of the first and second delay times and the comparison of the first and second associated frequencies, generating an indication that the via contains one or more of the group selected from: a void in a body of the via, a void at the bottom of the via, and no voids.

14. The method of claim 13, wherein an indication that the via contains no voids is generated if the first associated delay time is approximately equal to the expected delay time and the second associated delay time is approximately double the expected delay time.

15. The method of claim 13, wherein an indication that the via contains the void in the body of the via is generated if the first associated delay time is shorter than the expected delay time and the second associated delay time is approximately equal to the expected delay time.

16. The method of claim 13, wherein an indication that the via contains the void at the bottom of the via is generated if the first associated delay time is shorter than the expected delay time and the second associated delay time is approximately equal to double the first associated delay time.

17. The method of claim 13, further comprising, based on an indication that the via contains a void in a body of the via or a void at the bottom of the via, modifying the operation of one or more process tools to produce subsequent integrated circuit devices that have a lower likelihood of having voids.

18. A system for non-destructive acoustic metrology for void detection in a via in a sample, the system comprising:
a first source for generating a excitation beam directed towards the via in the sample;
a second source for generating a probe beam directed towards the via in the sample;
an optical sensor for detecting a reflected probe beam reflected from the sample;
at least one processor; and
a memory storing instructions, that when executed by the at least one processor, perform actions comprising:
generate a model for determining the existence of a void within the via, comprising:
generate a model signal representative of a signal that would be received from performing acoustic metrology on the via;
remove a signal component due to temperature rise and subsequent heat dissipation from the model signal;
generate a model periodogram by performing a Fourier transform over a sliding window;
apply a modified image processing segmentation algorithm to locate centroid locations of echo patterns in the model periodogram; and
generate a correlation of the centroid locations to a depth of where a model acoustic pulse was reflected within the via; and
analyze data associated with the reflected beam, using a detection periodogram, to determine one or more detection centroids;
compare features of the one or more detection centroids to expected features of the via to determine if there is a void in the via; and
if there is the void in the via, generating an indication that there is the void in the via.

19. The system of claim 18, wherein the via is a through silicon via (TSV) having a height to width ratio of approximately 10:1 and a depth of approximately 10-20 µm.

20. The system of claim 18, wherein the first source is a short pulse laser configured to generate a 532 nm wavelength laser beam, and the second source is a continuous wave laser configured to generate a 660 nm wavelength laser.

21. The system of claim 18, wherein the instructions, that when executed by the at least one processor, perform actions further comprising:

applying the generated correlation to determine the depth of an acoustic wave reflection associated with the one or more detection centroids; and
displaying the depth associated with the one or more detection centroids.

22. The system of claim 18, wherein the instructions, that when executed by the at least one processor, perform actions further comprising:
if there is the void in the via, diverting the sample from production for additional inspection; and
based on the additional inspection, modifying the operation of one or more process tools to produce subsequent integrated circuit devices that have a lower likelihood of having voids.

23. A substantially void-free integrated circuit device prepared by a process comprising the steps of:
manufacturing at least a portion of a first wafer using one or more process tools;
receiving the first wafer for inspection, wherein the first wafer includes multiple vias;
directing an excitation laser beam at a via of the multiple vias, such that an acoustic wave propagates through the via;
directing a probe laser beam at the via, such that the probe laser beam reflects off the sample, creating a reflected beam encoding data about propagation of the acoustic wave in the via;
analyzing, using a periodogram, the reflected beam to identify a first centroid and a second centroid, wherein the first centroid has a first associated delay time and a first associated frequency and the second centroid has a second associated delay time and a second associated frequency;
comparing the first and second associated delay times to an expected delay time for an ideally filled via;
comparing the first and second associated frequencies to an expected frequency range;
based on the comparison of the first and second delay times and the comparison of the first and second associated frequencies, determining that the wafer contains at least one void in one or more of the multiple vias;
diverting the first wafer from production for additional inspection;
modifying the operation of the one or more process tools to produce subsequent wafers that have a lower likelihood of having voids; and
manufacturing a second wafer using the modified operation of the one or more process tools to produce the substantially void-free integrated circuit device.

* * * * *